(12) United States Patent
Ringold et al.

(10) Patent No.: US 11,944,435 B2
(45) Date of Patent: Apr. 2, 2024

(54) SYSTEM AND PROCEDURE FOR STABILIZING, STORING AND RECOVERING BLOOD SAMPLES

(71) Applicant: VDI Laboratory, LLC, Simi Valley, CA (US)

(72) Inventors: Randy Ringold, West Hills, CA (US); Kyle Wilson, Simi Valley, CA (US); Tyson Ringold, Toronto (CA); Ekaterina Pesherov, Encino, CA (US)

( * ) Notice: Subject to any disclaimer, the term of this patent is extended or adjusted under 35 U.S.C. 154(b) by 922 days.

(21) Appl. No.: 16/622,040

(22) PCT Filed: Jun. 13, 2018

(86) PCT No.: PCT/US2018/037302
§ 371 (c)(1),
(2) Date: Dec. 12, 2019

(87) PCT Pub. No.: WO2018/231960
PCT Pub. Date: Dec. 20, 2018

(65) Prior Publication Data
US 2020/0170557 A1  Jun. 4, 2020

Related U.S. Application Data

(60) Provisional application No. 62/519,171, filed on Jun. 13, 2017.

(51) Int. Cl.
*A61B 5/15* (2006.01)
*A61B 10/00* (2006.01)
(Continued)

(52) U.S. Cl.
CPC .. *A61B 5/150358* (2013.01); *A61B 5/150305* (2013.01); *A61B 10/0096* (2013.01);
(Continued)

(58) Field of Classification Search
None
See application file for complete search history.

(56) References Cited

U.S. PATENT DOCUMENTS 3,819,106 A   6/1974   Schuster
5,489,614 A   2/1996   Korkolainen
(Continued)

FOREIGN PATENT DOCUMENTS

CN   100359314         1/2008
CN   100359314 C   *   1/2008
WO   WO-2005102526 A1 *  11/2005  .......... B01L 3/50825

OTHER PUBLICATIONS

International Search Report for corresponding application PCT/US2018/037302 (WO201831960).
(Continued)

*Primary Examiner* — Matthew D Krcha
(74) *Attorney, Agent, or Firm* — Mehdi Zamanpour

(57) ABSTRACT

Blood samples are maintained in a modified atmosphere sealed environment, where moisture is reduced using a desiccant and oxygen is removed using a deoxygenation compound, thus resulting in the preservation of numerous blood analytes, for delayed (e.g., 14 days from collection) blood testing, such as for enzymatic activity, concentration of protein and measurement of other blood components in human and veterinary blood test applications.

8 Claims, 15 Drawing Sheets

(51) Int. Cl.
  *B01L 3/00* (2006.01)
  *G01N 1/30* (2006.01)
(52) U.S. Cl.
  CPC .............. *B01L 3/5021* (2013.01); *B01L 3/505* (2013.01); *G01N 1/30* (2013.01); *A61B 2010/0006* (2013.01); *B01L 2200/18* (2013.01); *B01L 2300/0618* (2013.01); *B01L 2300/0809* (2013.01); *B01L 2300/105* (2013.01); *B01L 2300/123* (2013.01); *B01L 2300/126* (2013.01)

(56) References Cited

U.S. PATENT DOCUMENTS

| | | |
|---|---|---|
| 5,814,276 A | 9/1998 | Riggs |
| 5,866,007 A | 2/1999 | Whitson |
| D930,848 S | 9/2021 | Ringold |
| 2004/0137633 A1 | 7/2004 | Shin |
| 2004/0209059 A1 | 10/2004 | Foss |
| 2005/0082243 A1 | 4/2005 | Lahti |
| 2005/0227269 A1 | 10/2005 | Lloyd, Jr. |
| 2006/0194264 A1 | 8/2006 | Sheppard, Jr. |
| 2007/0208275 A1* | 9/2007 | Vinogradov ......... A61B 5/1411 600/584 |
| 2008/0047908 A1 | 2/2008 | Sekine |
| 2009/0227541 A1 | 9/2009 | Baker |
| 2011/0114881 A1 | 5/2011 | Torii |
| 2014/0087360 A1 | 3/2014 | Woodside |
| 2014/0227732 A1* | 8/2014 | Saqi ................... A61B 10/0283 435/29 |
| 2014/0295429 A1 | 10/2014 | Hogan et al. |
| 2016/0045148 A1* | 2/2016 | Al-Uzri .............. A61B 5/15144 600/583 |

OTHER PUBLICATIONS

Extended European Search Report for corresponding application EP18817633.3 (EP3639005).

* cited by examiner

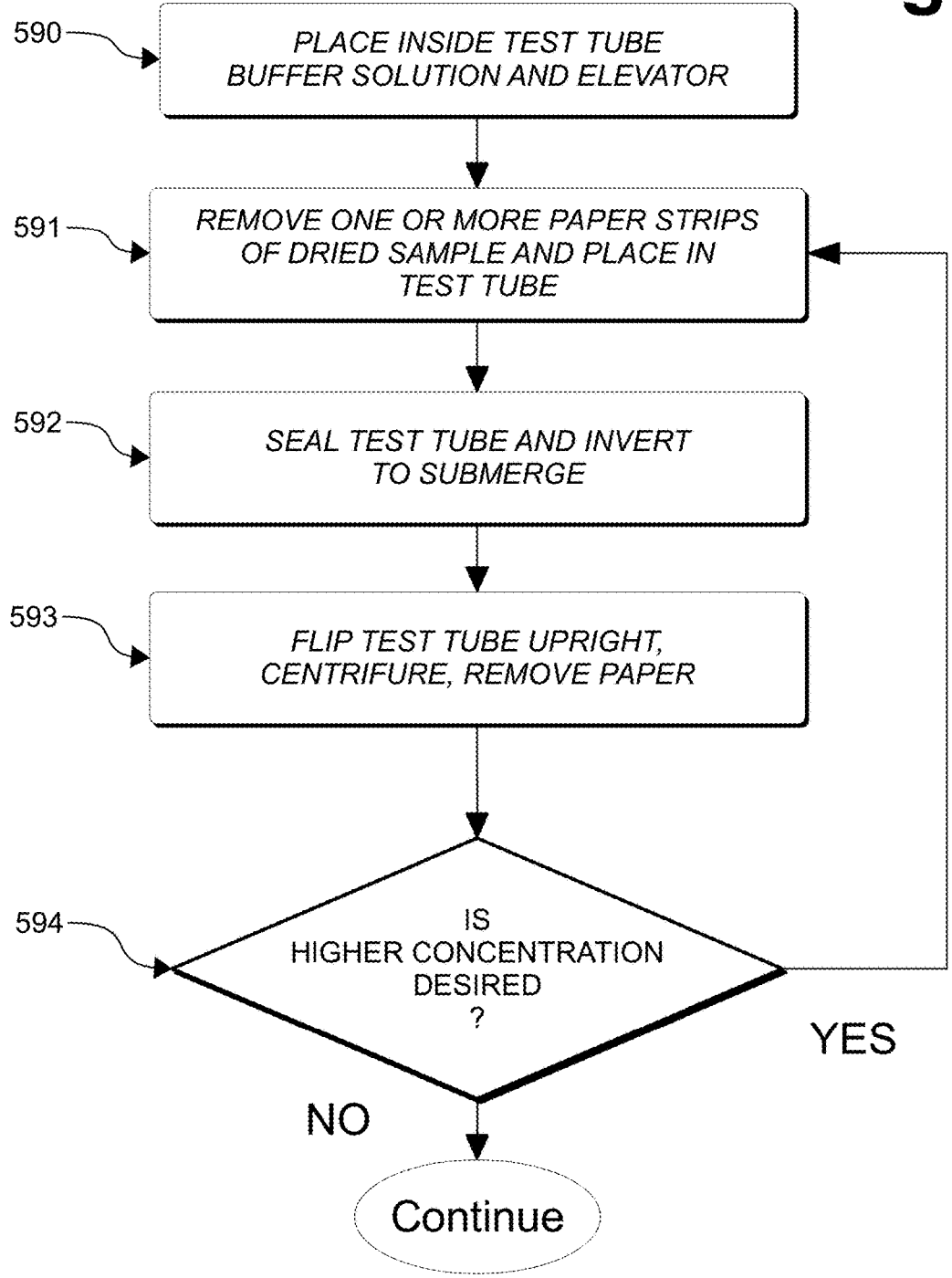

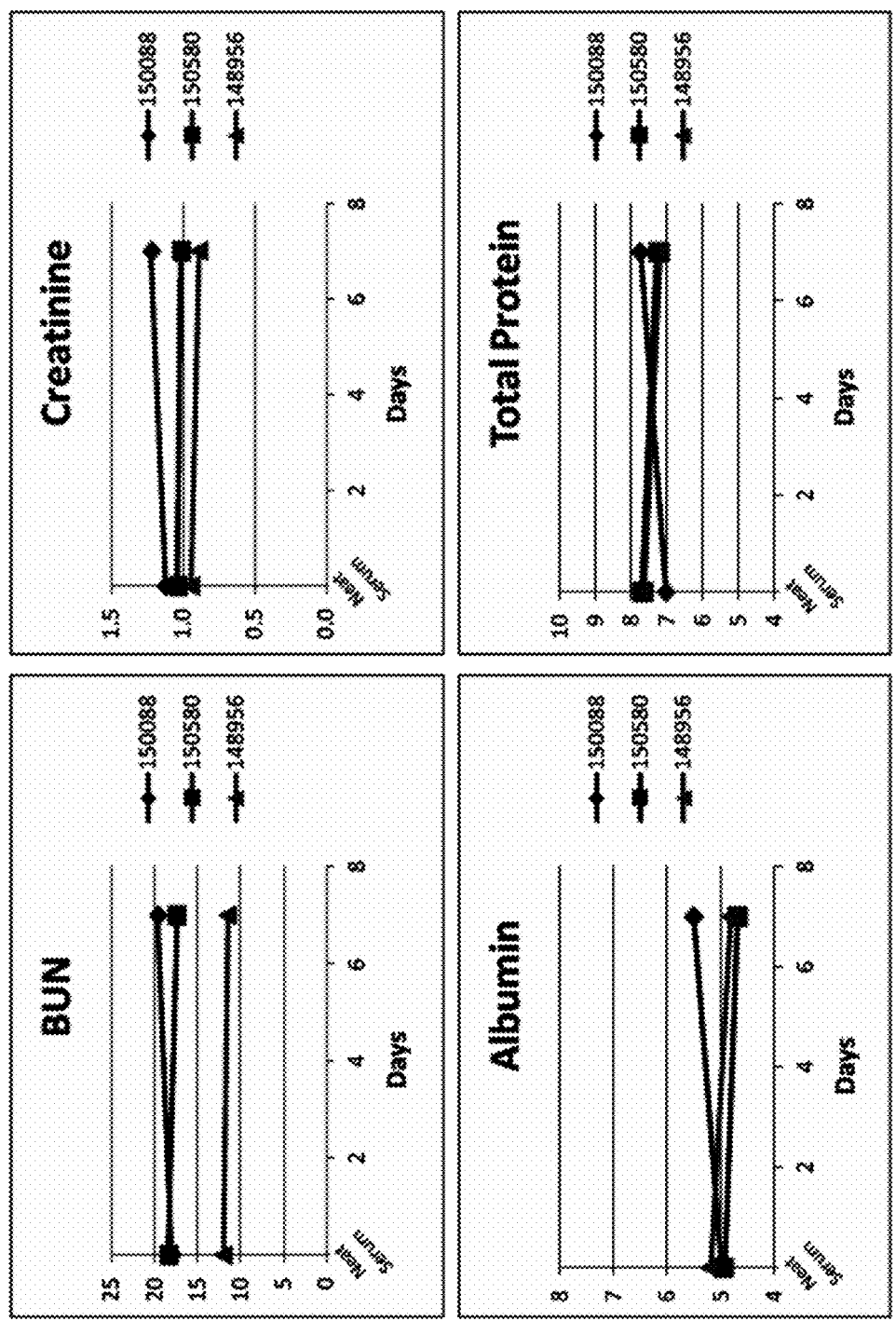

SYSTEM AND PROCEDURE FOR STABILIZING, STORING AND RECOVERING BLOOD SAMPLES

CROSS-REFERENCE TO RELATED APPLICATION

The present application is a national phase application of international patent application number PCT/US18/37302, filed on Jun. 13, 2018, that claims priority to U.S. provisional patent application No. 62/519,171 filed on Jun. 13, 2017, the content of each referenced application is included herein in its entirety by reference.

FIELD OF THE INVENTION

The invention relates to a method, apparatus, devices and system for handling blood samples, more specifically, the invention comprises a system and procedure for stabilizing, extracting and testing blood samples.

BACKGROUND OF THE INVENTION

Clinical laboratory testing typically involves liquid whole blood and/or liquid plasma, or serum. It is thus critical to preserve the integrity of blood samples from the location and time they are drawn to the location and time they are used.

Special preservatives and/or transportation procedures to preserve specimen integrity are required as proteolytic enzymes, naturally occurring in blood, plasma or serum, can degrade proteins. Routine commercial laboratories have set up extensive logistical networks to rapidly transport specimens. This includes, for example, shipping the specimens in insulated containers with cold packs or dry ice and/or tubes with special preservatives.

In the 1960s, dried whole blood testing was launched for neonatal testing of Phenylketonuria (PKU). Using special cellulose based paper, dried blood spot cards were used to collect blood samples for PKU testing. The specimens, once dried, assisted in the preservation of this analyte. The DBS cards could be stored and transported at ambient temperature for up to two weeks, which allows for transportation by common letter mail service, thus reducing cost of transportation. Upon receipt by the laboratory, blood in the specimen is extracted and tested for PKU.

Since that time, the use of dried blood spot collection and testing has expanded to test for other analytes, provided that certain requirements are met, which include, for example, that the analyte must be in relatively high concentration; the analyte must be very stable under adverse conditions and the analyte must not require a high degree of analytical precision to be useful.

Further, other manufacturers have developed similar devices using cellulose based paper and synthetic based papers for dried blood, serum, plasma testing, herein referred to dried blood specimen (DBS), however still suffer from the same limitations.

The prior art methods and devices meet the above limitations only for those applications that can be satisfied with low precision (e.g., genetic DNA testing). However the use of DBS for routine chemistries, enzymes, or high precision and/or high sensitivity work fails to meet the required specifications. In tests that measure enzyme activity, for example, enzymes often become inactive after being dried i.e. the enzymes do not convert substrate to product. In tests that use antibodies to measure protein mass (ELISA), drying specimens causes epitopes to become hidden or 3-dimensional conformation is lost i.e. antibodies fail to bind to the target protein. In tests that require a high degree of precision or sensitivity, consistent concentration of the DBS to near neat blood levels is not achieved i.e. unable to measure low concentration of a target analyte with satisfactory precision. The fundamental problems to be solved are:

- how to stabilize the specimen so enzymes would properly function
- how to maintain protein structure so immunoassays would properly recognize epitopes
- how to consistently concentrate the specimen to maintain precision and sensitivity Alternative materials, other than cellulose, have been developed. Synthetic materials have advantages over cellulose in greater recovery due to low non-specific binding. However due to the impact of specimen drying and prolonged storage (up to two weeks) at ambient temperature the inherent limitations of DBS still remain.

Another process that dries and stabilizes biological samples is lyophilization. Invented in the early 1900's, it was derived from a similar method used by the natives of the Andes. Lyophilization is a process of water removal by sublimation. Under a vacuum, liquid water is quickly frozen and the water is instantly turned into a gas and removed. The process is also known as freeze-drying.

Lyophilization is well known for its ability to preserve a wide range of biological samples. Pharmaceuticals, diagnostic reagents and calibrators, bacterial cultures, are frequently lyophilized. The end result is a dry sample that is under vacuum that can be stored. Studies performed since the nineteen sixties have shown that higher vacuum conditions result in longer storage time, presumably due to lower oxygen levels (Dewald, 1966). Because of the required logistics and the prohibitive cost, even as lyophilization is effective at sample preservation, the process is impracticable to implement as a routine use in blood sample preservation and diagnostics.

On other hand, DBS eliminates the time-sensitive nature of blood testing. It removes the high cost of packaging and shipping and allows for testing in situations that are poorly served today such as rural/undeveloped markets or home-based wellness screening. Because of these advantages, there has been a long-felt need to use DBS in testing for many analytes in blood samples. However all currently available DBS products and testing procedures do not overcome the inherent limitations of current DBS testing and thus prevents a widespread use to analytes other than the ones that meet the stability, concentration and precision limitations (as described above).

Therefore, there is a need for a method, apparatus and system that provide specimen stability for storage and transportation in a way that improves servicing the healthcare needs in a cost-effective manner.

SUMMARY OF THE INVENTION

The invention provides a method for stabilizing blood samples from the time the blood samples are drawn to the time the blood is extracted (recovered) for testing. The invention provides a system comprised of devices to collect blood samples, stabilize the samples, transport the samples and extract/recover blood for testing. The method and system of the invention allow blood, plasma or serum samples to be preserved for at least several weeks at ambient temperature and a process to extract the specimen at a concentrated, near neat, volume level. Implementations of the invention, disclosed herein, utilize dry blood, serum, plasma, specimen (DBS) techniques.

Blood samples are drawn from subjects and immediately stabilized by placing the samples in a deoxygenated and dehydrated environment. The medium that hosts the sample, a desiccant and an oxygen removing agent may be a sealed bag that is also suitable for storage and transportation in a form of a package. Once the package is received at a laboratory, blood components are extracted into a liquid medium suitable for testing.

The invention comprises a method for extracting and concentrating dried blood, plasma, or serum to near neat levels. Such extracted and concentrated specimen may be tested-as-usual as done using traditional liquid blood, plasma, or serum specimens. The invention uses in a dried format as a means to stabilize a wide range of analytes for measurement, cost effectively, for up to two weeks at ambient temperature. The DBS requires an effective and reproducible extraction process.

The goal of the extraction process is to rehydrate and dislodge blood, plasma, or serum components from the DBS fiber matrix. Extraction fluid is used to re-suspend blood, plasma, or serum components.

Implementations of the invention may be practiced in human and veterinary diagnostics to draw, stabilize, store and/or transport blood samples for testing.

As detailed below, the invention may be embodied to satisfy the requirement of any blood test application that requires storage and extraction of analytes from a blood sample. However, in addition to the enzyme detection, protein concentration, and other analytes measurements specifically tested and presented in this disclosure, one with ordinary skills in the pertinent art may use embodiments of the invention as disclosed directly, simply by first performing a test-run to check for accuracy. The embodiment of the invention may be used once stability requirements are satisfied. A test-run may consist in simply by drawing two sets of samples of blood: a first set is tested for a given analyte immediately after drawing the sample, and the second set is tested after it has been preserved for a given period of time according to an embodiment of the invention. Accuracy can easily be determined by comparing the results from the first set to the results of second set.

In other instances, the invention may be adapted in accordance with the invention to a specific analyte of concern. For example, embodiments of the invention may be adapted for tests that determine viral load in patients. The stability of viral load in a blood sample is an important pre-analytical variable that affects the accuracy of viral pathogen quantitation. Once a blood sample is drawn from a patient, it must be handled in a manner that preserves viral load in the sample. Embodiments of the invention may utilize stabilizing reagents to not only inactivate the viral agent but also stabilize the viral nucleic acids for accurate viral load determination.

BRIEF DESCRIPTION OF THE DRAWINGS

FIG. 5E is a flowchart diagram representing steps in the method of extracting near neat-level blood samples, in accordance with an embodiment of the invention.

FIG. 6G shows the measurement of TK1 in five different subjects using an air dry in ambient temperature

FIG. 11 is a plot diagram showing the result of testing blood urea nitrogen (BUN) level in three subjects from samples that were stored for a period of seven (7) days.

FIG. 12 is a plot diagram showing the result of testing blood creatinine level in three subjects from samples that were stored for a period of seven (7) days.

FIG. 13 is a plot diagram showing the result of testing blood albumin level in three subjects from samples that were stored for a period of seven (7) days.

FIG. 14 is a plot diagram showing the result of testing blood total protein level in three subjects from samples that were stored for a period of seven (7) days.

DETAILED DESCRIPTION OF THE INVENTION

Figure 1A:
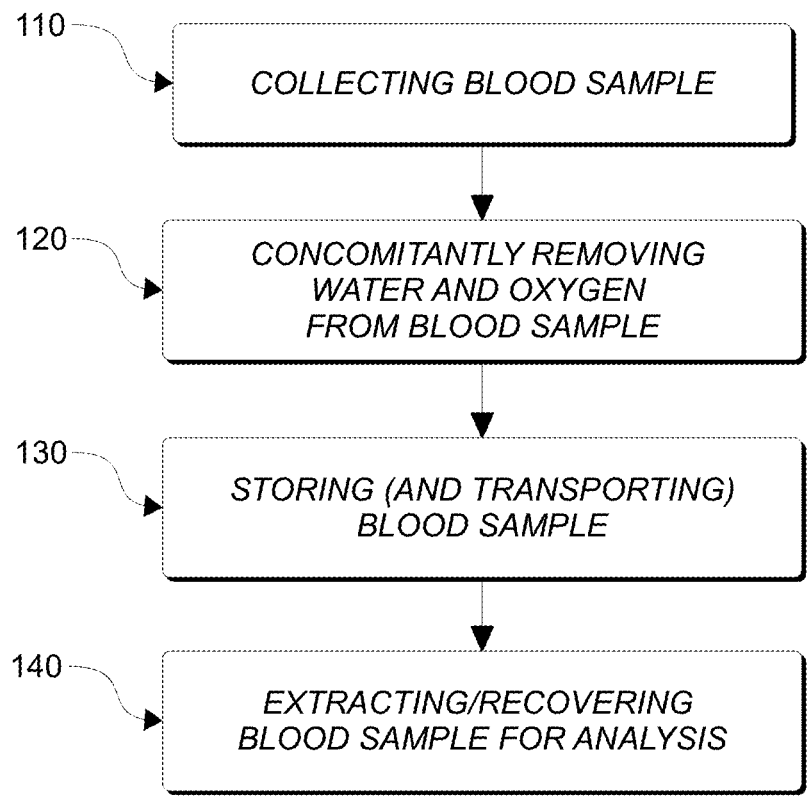
FIG. 1A illustrates steps in the procedure for drawing blood sample, preserving and extracting blood samples for testing in accordance with an embodiment of the invention.

The invention provides a method for stabilizing blood samples from the time the blood samples are drawn to the time the blood is extracted (recovered) for testing. The invention provides a system comprised of devices to collect blood samples, stabilize the samples, transport the samples and extract/recover blood for testing. The method and system of the invention allow blood, plasma or serum samples to be preserved for at least several weeks at ambient temperature and a process to extract the specimen at a concentrated, near neat, volume level. Implementations of the invention, disclosed herein, utilize dried blood, serum, plasma specimen (DBS) techniques.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention. The claims following this description are what define the metes and bounds of the invention.

Terminology

Throughout the disclosure, a reference to blood sample comprises a reference to a sample of blood or whole blood including plasma and all of the cellular components such as red and white blood cells. Plasma shall refer to the liquid phase of blood less the cellular components. Serum shall mean the fluid separated from clotted blood (e.g., plasma less clotted proteins). In addition, a reference to sample, as a shorthand reference, shall refer to any of the latter terms, the specific meaning of which depends on the context in which it is used and can be easily inferred by one with ordinary skills in the art.

Dried blood, serum, plasma specimen (DBS) shall refer to any means for obtaining dried samples of blood, plasma, or serum. This shall include both cellulose-based and synthetic fiber-based products. These carrier fibers act as the transport medium of the specimen in the dried format. The fibers are manufactured to retain a reproducible amount of volume per unit area. This allows for a known volume of retained specimen prior to drying.

Neat or neat volume shall refer to the concentration of blood components in their native liquid state. Routine blood, plasma, or serum testing begins with the sample in its native liquid state. The procedure may require a dilution prior to testing; however components that are low in concentration do not. To achieve sensitive and reproducible results the extracted fluid from the DBS needs to be at or close to neat blood, plasma, or serum level.

Modified atmosphere packaging (MAP) shall mean a system to artificially create an atmosphere separated from the ambient atmosphere and resistant to gas exchange. MAP may be a bag, container or device and made from materials that are gas impermeable such as plastic or glass.

Anti-oxidant treatment shall mean methods to remove residual molecular oxygen ($O_2$) from a modified atmosphere packaging (MAP). The amount of anti-oxidant required shall reduce the level of residual $O_2$ within the MAP to less than 0.01%.

The term "oxygen scavenger" is used throughout the disclosure to refer to anti-oxidant compounds known for biding (and even reacting) with molecular oxygen, which results in fixating the oxygen in a non-gaseous state.

A desiccant refers to any compound that is known to bind water molecules. Desiccant treatment shall mean methods to remove residual $H_2O$ from a modified atmosphere packaging (MAP).

Extraction shall mean the process of removing the blood components from the fiber matrix, whether cellulose or synthetic based. The fluid used to extract the specimen may vary depending upon the tested analyte.

General Concept of the Procedure and System

Applicant suspects that several factors lead to the degradation of blood samples within DBS. A variable amount of moisture exists in air and can contribute to the degradation. With sufficient moisture, proteolytic enzymes, naturally occurring in blood, plasma or serum, can degrade proteins. The presence of oxygen, a highly reactive oxidative species, can alter organic compound structure. Further, in the presence of moisture, carbon dioxide can turn into carbonic acid and degrade proteins and other blood components.

Embodiments of the invention achieve the stabilization of analytes in blood samples by removing a substantial portion of the water and oxygen from the blood sample, and maintaining such an environment in which the blood sample is stored until the blood sample is extracted/recovered for testing. The invention applies a desiccation compound and an oxygen scavenger compound within a sealed impermeable environment. The two compounds act concomitantly where the desiccant removes the moisture from the blood sample while the oxygen scavenger acts to remove oxygen. Because the oxygen scavenger may require a given level of humidity to achieve an effective level of deoxygenation, embodiments of the invention utilize desiccants that act within a time range during which humidity level is adequate for the oxygen scavenger to remove oxygen from the environment of the blood sample. The desiccant then continues to act on the air surrounding the blood sample to reach a desired dehydration level.

FIG. 1A illustrates steps in the procedure for drawing blood sample, preserving and extracting blood samples for testing in accordance with an embodiment of the invention. Step 110 represents the step of collecting a sample of blood. The latter step is conducted in accordance with standard practices for drawing blood (e.g., from a human or an animal subject) and obtaining a sample (e.g., dried blood specimen). The methods for drawing blood and obtaining a sample, as widely known to one with ordinary skills in the medical (or the veterinary) field are considered part of the implementation of the invention, are well known, and do not require a detailed description in the present disclosure.

Step 120 comprises creating an environment around the blood sample created in step 110 in which oxygen is removed concomitantly while moisture is reduced. At step 120, a blood sample may be sealed in a bag that is air tight, and is impermeable to both oxygen and water.

Step 130 comprises packaging the blood sample for storage and/or transportation. Step 130 may comprise, in addition to the deoxygenation and dehydration of step 120, further conditioning the environment of the package, such as insulating the blood sample for protection from extreme heat during transport.

Step 140 comprises extracting the blood sample (whole blood or serum) to near neat levels for testing.

Figure 1B:
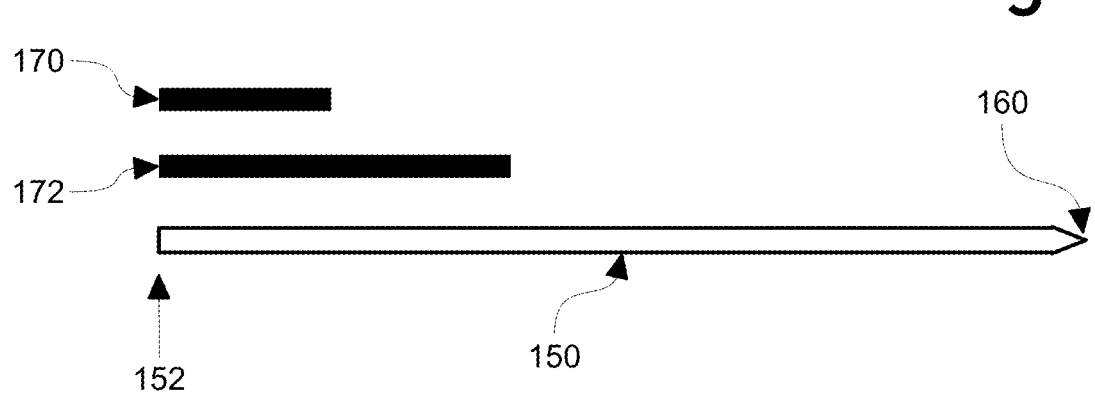
FIG. 1B illustrates a unique timing feature of an embodiment of the invention, whereby deoxygenation is designed to occur within a time frame during which moisture remains at a sufficient level, as required by an oxygen scavenger in use.

FIG. 1B illustrates a unique timing feature of an embodiment of the invention, whereby deoxygenation is designed to occur within a time frame during which moisture remains at a sufficient level, as required by an oxygen scavenger in use. Time arrow 150 represents the time period between the drawing of the blood sample 152 and the extraction 160. Immediately following blood draw, the sample is placed in a sealed environment with a desiccant and an oxygen scavenger. The oxygen scavenger starts acting immediately and achieves a desired level of oxygen removal with a time period 170 (e.g., 1 hour). The desiccant also starts acting immediately, but the action time 172 is much slower than of the oxygen scavenger.

Prior art methods and systems for preserving biological products have been known and practiced for many decades. In the food industry it is common practice that in order to preserve the freshness of the food, exposure to air must be reduced to reduce oxidation and to water to reduce microbial activity. The methods used in the food industry typically struggle to preserve moisture in the foods (as a desired indicator of freshness). Deoxygenation is achieved simply by replacing the air surrounding the foods with an inert gas.

In applications where preserving freshness is not the target outcome, such as preserving dry meats, desiccants (e.g., salts) are applied directly to the foods regardless whether the desiccant will affect the molecular structure of the foods.

Therefore, although deoxygenation and dehydration have been known to reduce biological degradation of biological products, and although preserving/stabilizing blood samples for testing has been needed for many decades, including preserving dried blood samples, applying deoxygenation and dehydration to achieve blood sample stabilization have eluded practitioners in the field of medical and veterinary blood testing. The invention teaches a method and system for preserving blood samples in a manner that expands the use of blood sample stabilization for testing of numerous different analytes in the blood.

Components and Processes

A system embodying the invention comprises blood, plasma, or serum collection devices. The collection devices may consist of various configurations to contain the blood, plasma, or serum upon absorbent paper which may be cellulose or synthetic based.

Embodiments of the invention may utilize existing devices for collecting blood, storing, transporting and extracting blood samples for testing. However, unlike prior art systems, the drying of collected blood samples, according to the invention is carried out concomitantly with the scavenging of oxygen in the samples' environment. The system further comprises at least one oxygen scavenger and at least one desiccant. The procedure, according to the invention, teaches a practitioner how to combine the desiccant and oxygen scavenger in a sealed environment in order to create an optimal condition that preserves blood samples.

Blood, plasma, or serum collection paper that may be cellulose or synthetic based. Blood, plasma, or serum is placed onto the paper in a fashion to allow free flow and retention within the matrix of the fibers. The fibers are designed to retain a set and reproducible amount of fluid and let to air dry. This becomes the DBS. As an alternative to air drying, the collection device and/or the MAP may contain sufficient desiccant to absorb all water from the sample allowing for the collection device to be inserted into the MAP wet rather than air dry.

Figure 2A:
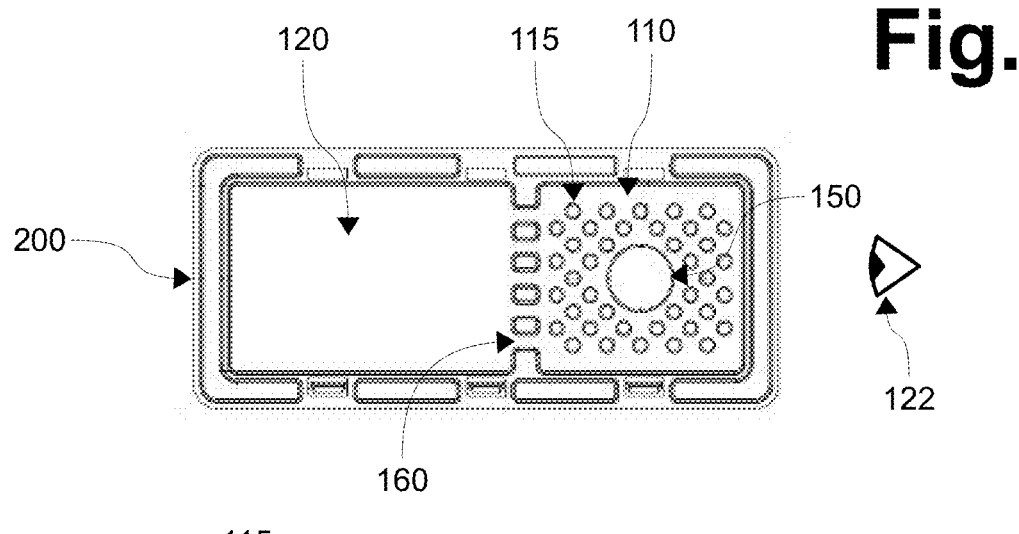
FIG. 2A is a top view of a device for collecting and storing blood, plasma, or serum.

FIGS. 2A, 2B, 2C and 2D depict a custom collection device for collecting, storing and transporting blood samples. FIG. 2A is a top view of a device 200 for collecting and storing blood, plasma, or serum. Device comprises an enclosure that contains a region 110 for the synthetic absorbent paper and a region 120 for the desiccant to dry the specimen. There is a hole 150 above the absorbent paper that allows specimen to be added directly upon it. There are channels 160 between the absorbent paper and desiccant to allow free air flow between the compartments. There absorbent paper is lifted off the plastic enclosure by the addition of small raised numbs 115 to further aid air flow between the absorbent paper and desiccant. The goal is to minimize contact with the enclosure and aid in fast drying.

Figure 2B:
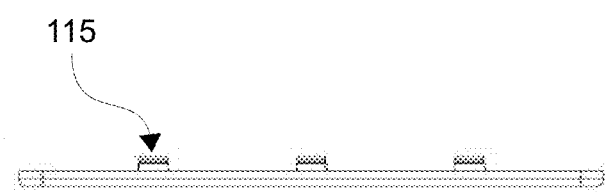
FIG. 2B depicts a lateral view of the part depicted in FIG. 2A.

Point of view 122 indicates the point of view for representing a lateral view as depicted in FIG. 2B.

FIG. 2B depicts a lateral view of the part depicted in FIG. 2A. FIG. 2B highlights in particular the numbs 115 that allow for creating a volume that promotes air circulation.

Figure 2C:
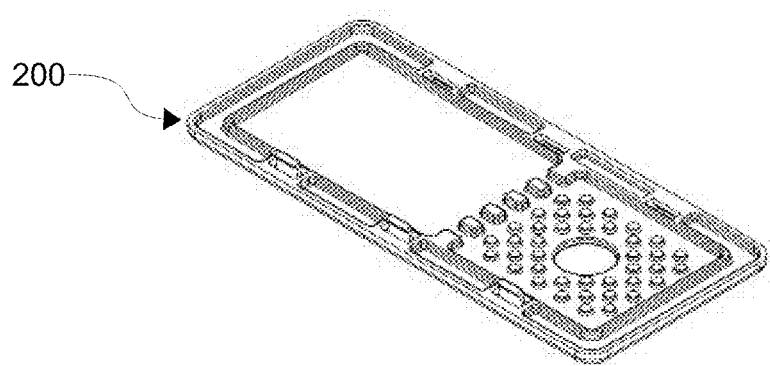
FIG. 2C depicts a perspective view of the device part depicted in FIG. 2A.

FIG. 2C depicts a perspective view of the device part depicted in FIG. 2A. FIG. 2C highlights in particular the volumetric aspect of the inside of device 200 which offers channels 160 that allow for air circulation.

Figure 2D:
FIG. 2D depicts a device for collecting and storing blood, plasma, or serum that may be designed to snap together to form an enclosure.

FIG. 2D depicts a device that may be identical as part 200 and may be designed to snap together with part 200 forming an enclosure. Desiccant is placed in one region 120; synthetic absorbent paper in the other 110. Once the enclosure is snapped together the absorbent paper is suspended above the enclosure via the raised bumps and available for sample placement through the hole 150.

The absorbent paper is fixed in size and has uniform pore size therefore a fixed amount of blood, plasma, or serum is contained within. For a higher level of precision, a volumetric pipette can be used to pipette an exact amount of blood, plasma, or serum into the device. Upon receipt by the lab, the paper is removed and eluted representing a fixed amount of blood, plasma, or serum.

The above design may be adapted to scale up or down the amount (or size or thickness) of paper that can capture a higher/lower amount of blood, plasma or serum. For example, multiple absorbent papers in a rack or a larger paper size in a larger enclosure can capture a higher amount of blood, plasma or serum. The custom collection device may be modified from these specifications for larger or smaller sample volumes, different types of absorbent paper for targeted applications, or other size variations while meeting any specification (e.g., USPS regulations 201 for common letter service) for storage, transportation, extraction or any other application.

Figure 3A:
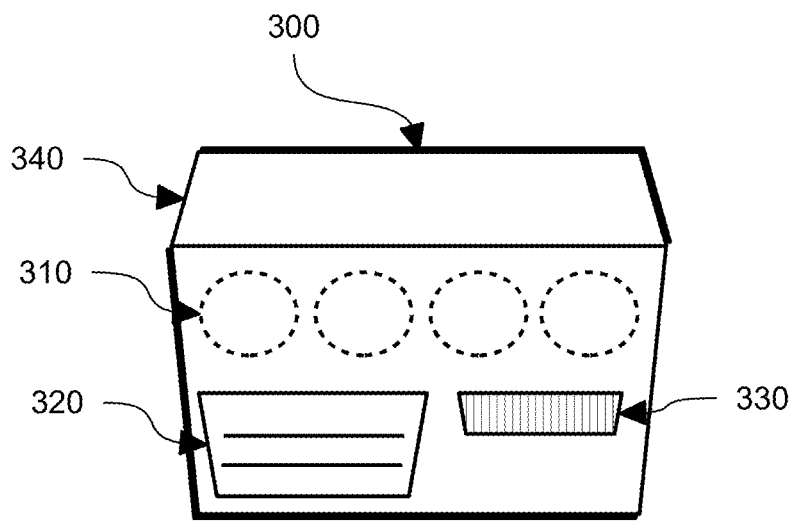
FIG. 3A generically depicts commercially available dried blood spot cards typically used for neonates.

Embodiments of the invention may utilize cellulose dried blood spots cards. FIG. 3A generically depicts commercially available dried blood spot cards typically used for neonates. A card 300 is cellulose based and has been commercially available since the 1960s. Blood, plasma, or serum is added to the card and the fluid spread across the paper. The pores 310 are fixed in size and therefore hold a fixed amount of blood, serum or plasma is contained per unit area. Upon receipt by the lab, precise punches are taken and eluted representing a fixed amount of blood, plasma, or serum. Card 300 typically has an area 320 for recording biographical data, and a unique identifier 330 (e.g., a serial number and/or bar code) for uniquely identifying and tracking the sample. Moreover, card 300 comprises a flap 340 for folding unto the rest of card for protection of the sample during storage and/or transportation.

Figure 3B:
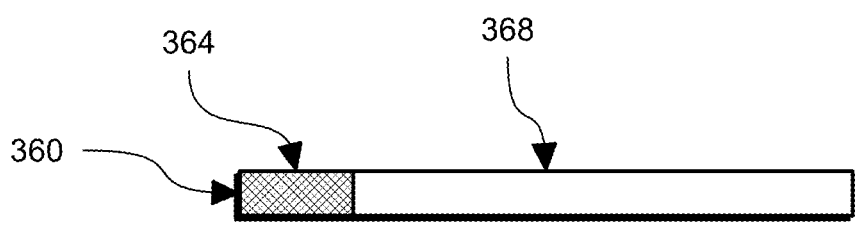
FIG. 3B generically depicts a synthetic fiber sticks.

FIG. 3B generically depicts a synthetic fiber sticks. A stick 360 affixes synthetic absorbent paper 364 onto plastic backing 368 for ease of use. The absorbent paper 364 is fixed in size and has uniform pore size therefore a fixed amount of blood, plasma, or serum is added via dipping into the specimen and absorbing via capillary action. Upon receipt by the lab, the sticks are eluted representing a fixed amount of blood, plasma, or serum.

Figure 3C:
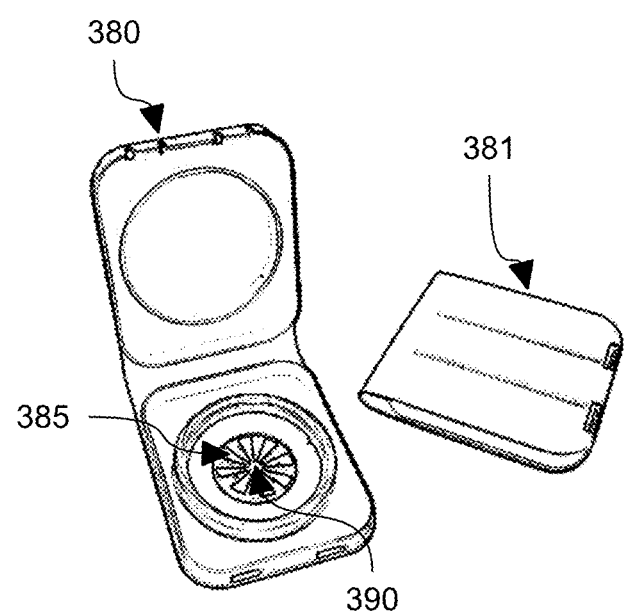
FIG. 3C depicts a synthetic fiber wedges device for use in an embodiment of the invention.

FIG. 3C depicts a synthetic fiber wedges device for use in an embodiment of the invention. Device 380 contains synthetic fiber wedges 385. Blood, plasma, or serum is placed down the center 390 and absorbed out to the absorbent paper wedges 385. The absorbent paper wedges are fixed in size and have uniform pore size therefore a fixed amount of blood, plasma, or serum is contained within. Upon receipt by the lab, the wedges are removed and eluted representing a fixed amount of blood, plasma, or serum. Device 380 may be designed to be closed to protect the blood sample, as shown in 381.

Modified Atmosphere Packaging (MAP)

Figure 4:
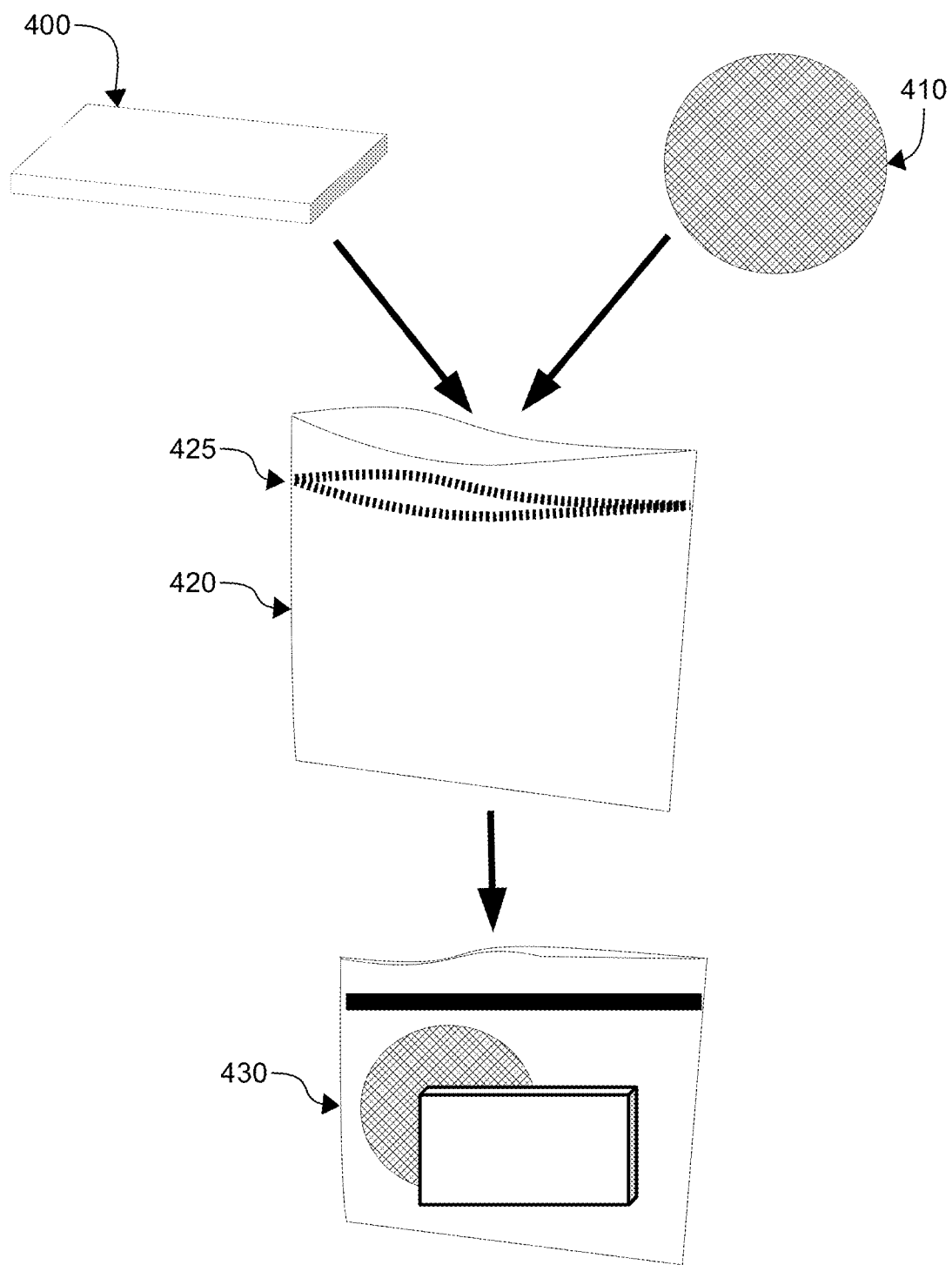
FIG. 4 represents the process for creating a modified atmosphere packaging that provides deoxygenation and dehydration in accordance with the teachings of the invention.

FIG. 4 represents the process for creating a modified atmosphere packaging that provides deoxygenation and dehydration in accordance with the teachings of the invention. Immediately following collection of a blood sample, using one or more collection devices (as described above), the collection device(s) 400 is/are placed in a modified atmosphere packaging 420: a package to artificially create an atmosphere separate from the ambient atmosphere and resistant to gas exchange. MAP may be a bag, container or device made from materials that are gas impermeable such as plastic or glass.

A plastic bag such as 420 comprises a seal 425 that allows for a tight closure of the bag. An example of bag may be commercially available Mylar bag impermeable gas exchange.

To prevent the oxidation of blood components within the MAP, an anti-oxidant is placed to eliminate residual $O_2$. The anti-oxidant can be any compound that binds and removes residual $O_2$. Such common commercially available compounds, such as iron powder, ascorbic acid, ascorbate salts, catechol, etc, bind the free oxygen and prevent the auto-oxidation of organic molecules.

Further to assist in the blood, plasma or serum drying and to prevent carbon dioxide turning into carbonic acid, a desiccant is placed within the MAP. Such common commercially available compounds, such as silica, montmorillonite clay, or synthetic zeolite, remove any moisture within the MAP during transportation.

Component 410 represents one or more containers containing one or more compounds capable of absorbing (also known as scavenging) oxygen. Component 410 also represents one or more containers for containing one or more desiccants. For practical reasons, a practitioner may choose to add a desiccant in the MAP, in addition or instead (as the case may be) to the desiccant that may be contained in the collection device 400.

Depending upon the type of absorbent paper product used the placement of the desiccant and oxygen absorber may be different. In some instances they may be within the collection device itself; in other instances they may reside in the MAP.

The end result is that within a short period of time both oxygen and moisture must be eliminated within the MAP for specimen stability to be achieved. Container 430 represents a bag that can be placed in a shipping package and/or store for later extraction of the blood sample.

An example may be a collection device (e.g., as represented in FIGS. 2A-2D) fitted with synthetic paper and molecular sieve as the desiccant. After a blood sample is placed onto the synthetic paper it is inserted into a Mylar bag that has an oxygen impermeable seal, and contains an oxygen scavenger. The oxygen scavenger is iron filings and reacts with the oxygen in the air to make ferrous oxide. This reaction occurs quickly in the presence of moisture to remove all oxygen (within 1 hour). Molecular sieve works slower but is able to draw and retain all moisture (within 2 hours).

The blood sample dried and stabilized are stored and/or shipped to a different location for delayed testing. Prior to testing the blood analytes, the dried blood is recovered/extracted back into a liquid solution.

It is the subject of the invention to provide a unique method and system to extract/recover blood samples that have been attached to an absorbent medium. The extraction method relies on the use of an elevator located within a test tube. In the prior art methods, the absorbent medium is placed in the buffer solution inside a test tube, the test tube is then shaken to promote the dissolution of blood analytes in the buffer. Prior art methods result in the dissolution of the analytes upon extraction. On the contrary, extraction according to the invention results in near neat level blood samples and even a higher concentrations if so is desired, as described below.

Figure 5A:
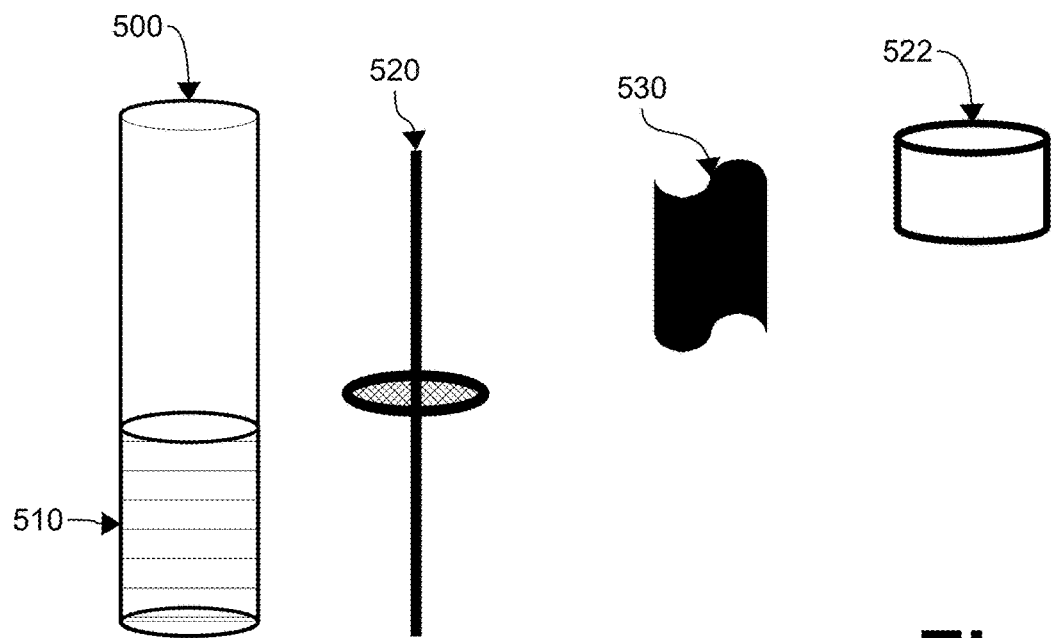
FIG. 5A depicts a test tube, a buffer solution, an elevator, a cellulose or synthetic paper carrying a blood sample and lid/cap for closing the test tube.

FIGS. 5A, 5B, 5C, 5D and 5E represent components of a system and a method of use thereof for extracting/recovering near neat level blood sample, in accordance with an embodiment of the invention. FIG. 5A depicts a test tube 500, a buffer solution 510, an elevator 520, a cellulose paper carrying a blood sample 530 and lid/cap for closing the test tube. The DBS paper elevator elevates the cellulose or synthetic paper punches, strips, wedges, or rectangle, within the micro-centrifuge tube 500.

In embodiments of the invention, DBS paper may be cut in one of several shapes. The test tube and elevators may be selected to accommodate for the shape of the paper. Devices selected to accommodate for the different shapes are considered part of any implementation of the invention.

Figure 5B:
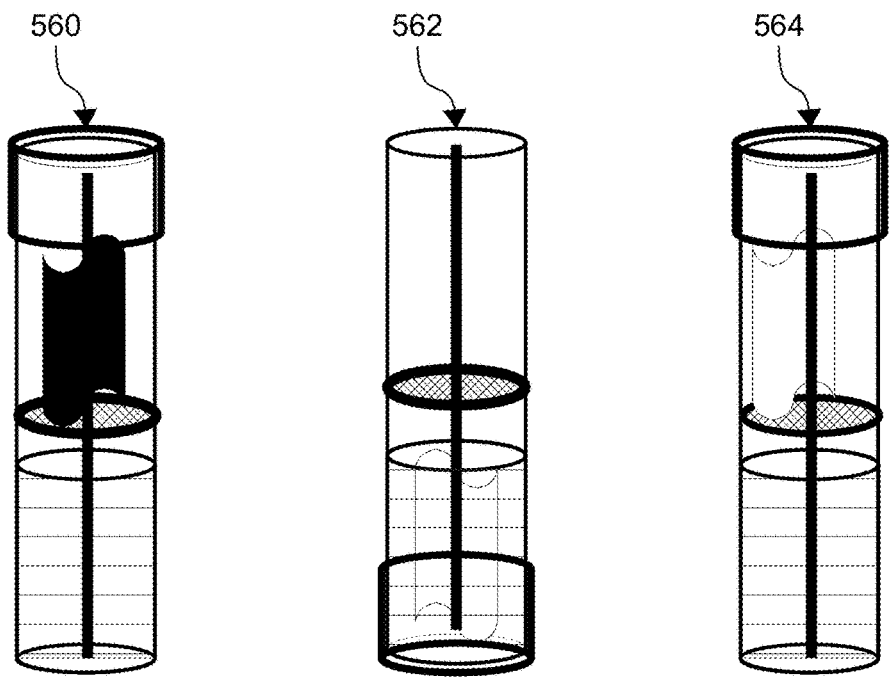
FIG. 5B represents the process of separating the blood components from the DBS paper.

FIG. 5B represents the process of separating the blood components from the dried blood specimen paper. To effectively remove the blood components from the DBS fibers, the paper is elevated above the bottom of the test tube 500 by use of the DBS paper elevator 520. Centrifugal force is then applied and the blood, plasma, or serum components are effectively extracted.

Upon receipt by the laboratory, a fixed and reproducible amount of DBS paper shall be obtained. The amount of paper can be punched or accurately provided prior to use by the user. The paper can be on cards or adhered to plastic sticks for easy handling. This fixed and reproducible amount of paper is placed within an enclosed tube 500 containing the DBS paper and elevator 520, as depicted in 560, 562 and 564. The DBS paper elevator raises the paper above the bottom of the test tube. An amount of extraction fluid or phosphate buffered saline 510 is placed into the tube.

Typically phosphate buffered saline works for most applications, although it may not work for measuring sodium or chloride due to the added salt. In some instances special buffered solutions may optimize recovery of the tested analyte. These solutions are typically used to make specimen dilutions and are detailed in the laboratory protocol from the manufacturer of test kits. Any reference to extraction fluid shall mean phosphate buffered saline and/or manufacture specified sample dilution fluid for the tested analyte.

Appropriate elution buffer is placed into the mico-centrifuge tube, paper and elevator inserted, and the capped tube is inverted. The tube is allowed to incubate to draw the elution buffer into the paper via capillary action. The amount of fluid can be the same amount as the original amount of blood, plasma, or serum applied if neat concentration is desired, or, a larger volume if a dilution is required. The tube is capped. The capped tube is inverted and centrifuged to bring all fluid and paper in contact with the cap (e.g., 562). The inverted tube is allowed to stand for a fixed amount of time. This time may vary by analyte to be recovered but typically requires 30 min to 1 hour. The fluid within the tube cap is absorbed by the paper through capillary action.

After incubation, the tube is centrifuged again bringing all fluid to the bottom of the tube. The DBS paper elevator maintains a proper distance from the tube bottom and with centrifugal force removes all fluid from the DBS paper, as represented in 564.

The DBS paper elevator is removed from the tube and testing occurs as usual. If a higher concentration is required the procedure can be repeated with a new dry sample from the same patient and the extract from the original extraction resulting in twice the original concentration.

Depending upon the amount of fluid added, dilution factors are applied to the final result, or, are part of the testing protocol compensating for the dilution.

Testing is then carried according to the guidelines to test for a specific analyte in question.

Figure 5C:
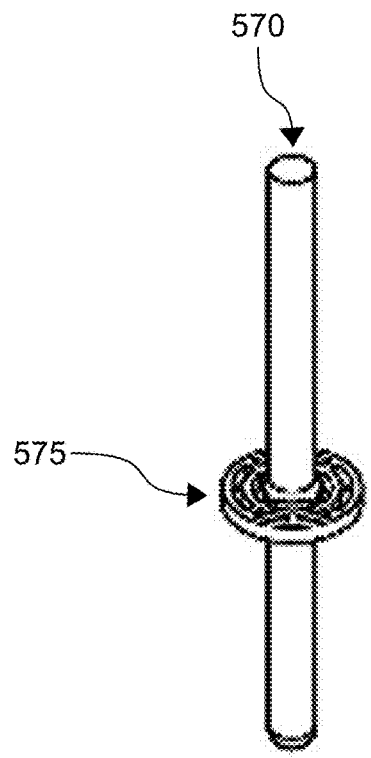
FIG. 5C represents elevators that may be utilized in test tube for extraction of near neat level blood samples, in accordance with an embodiment of the invention.

FIG. 5C represents elevators that may be utilized in test tube for extraction of near neat level blood samples, in accordance with an embodiment of the invention. Elevator 570 is designed such that paper strips may be wrapped around a top portion of the elevator, which becomes a bottom portion, submerged in the buffer solution, during incubation. Elevator 572 represents a designed that adequate for holding paper punches. In any designed according to the invention, an elevator possess a middle section (e.g., 575) that fits within the diameter of the test tube and has holes for passing liquids (e.g., blood) from one side of the test to the other while retaining paper on one side only. Numerous implementations of the elevators, according to the invention, may be fabricated and used with any size of test tube.

Figure 5D:
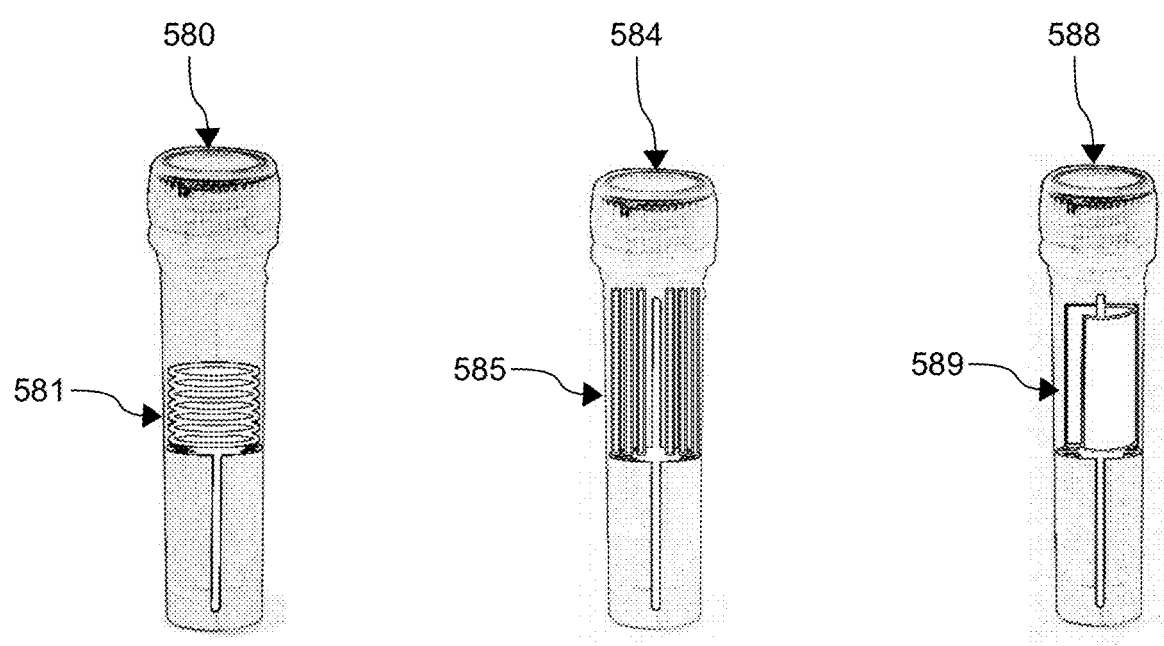
FIG. 5D represents several options for use of the elevator within the test tube for carrying out extraction, in accordance with embodiments of the invention.

FIG. 5D represents several options for use of the elevator within the test tube for carrying out extraction, in accordance with embodiments of the invention. Test tube 580, for example, is represented in FIG. 5D as carrying an elevator of type 572, whereas test tubes 584 and 588 are both carrying an elevator of type 570.

It is an important feature of the invention that an implementation of the invention allows for obtaining a higher concentration of blood analytes during extraction than it was initially present in the blood sample. For example, by stacking paper punches 581 in test 580, or strips 585 in test tube 584 or rectangles 589 in test tube 588.

FIG. 5E is a flowchart diagram representing steps in the method of extracting near neat-level blood samples, in accordance with an embodiment of the invention. Step 590 represents the step of preparing the test tubes by providing an appropriate amount of a buffer solution placed inside the test tube. An appropriate elevator is placed within the test tube.

Step 591 represents the step of removing the papers holding dried blood samples from the dried blood devices, selectively preparing paper punches, rectangles or strip (depending on the application being executed), and placing the paper in the test tube. The paper remains in the top portion of the of the test tube due to the presence of the elevator. Then at step 592, the test tube is sealed to prevent leakage of fluids, and flipped/inverted in order to bring the paper in contact with the buffer solution. The test tubes are incubated for a preset period of time (e.g., 1 hour). After a period of incubation, which allows the analytes in the dried to be diluted in the buffer solution. The test tubes are flipped back where the caps are at the top, at step 593, the test tube are centrifuged, which brings all liquid toward the bottom of the test tubes, then the paper is removed.

Step 594 is an important feature of the invention, as it allows a user to decide whether a higher concentration of an analyte is desired. If the user so chooses, then the test tubes, having the buffer solution used to extract blood samples, is used anew (e.g., step 591) to load one or more papers of dried blood, and the process is repeated, which yields a higher concentration of blood analytes. The latter important feature is very beneficial for testing analytes that may exist in extremely small concentrations in the blood, or for which the detection techniques may require a higher concentration.

Test Results of Analytes Using Embodiments of the Invention

Embodiments of the invention have been used to test for a plurality of analytes to assess the efficacy to preserve analytes in blood samples. For each selected analyte, neat serum is compared to aged (several days/weeks old) samples on a number of different patients.

Thymidine Kinase, Type 1 (TK1).

TK1 is an enzyme that makes the nucleic acid thymine. The enzyme exists in minute concentrations in normal healthy individuals. The method for measurement is an indirect, modified two-step, competitive chemiluminescence immunoassay (CLIA) for the quantitative determination of TK1 in human serum and EDTA plasma. The assay utilizes an initial enzymatic reaction in which TK1 in the sample converts AZT (3'-azido-3'-deoxythymidine) to AZTMP (3'-azido-3'-deoxythymidine mono phosphate), this is followed by a competitive immunoassay for the quantitative determination of AZTMP. The amount of AZT converted to AZTMP is a measure of the amount of TK1 present in the sample. TK1 represents many analytical challenges. The methodology consists of an enzymatic step, a low level of detection, and a competitive immunoassay.

For point of reference, using prior art and following generally accepted methods to dry and test DBS samples, TK1 activity declines over time with an average decline of about 50% in 3-5 days. The exposure to atmospheric air (oxygen) and moisture quickly degrades TK1 activity.

For the purpose of testing the efficacy of the method and system of the invention, blood samples were drawn from several canine subjects. A sample from each subject was tested immediately after the blood draw and several other samples were stored according to the invention, and the TK1 test was carried out at several time intervals.

First, to make a clear comparison between an implementation of the invention and prior art methods, a set of blood samples was stored according to prior art methods, another set was air dried without removal of oxygen, another set of blood samples was stored in the presence of a desiccant but without removing oxygen from its surrounding and lastly another set was stored in accordance with an implementation of the invention.

Figure 6A:
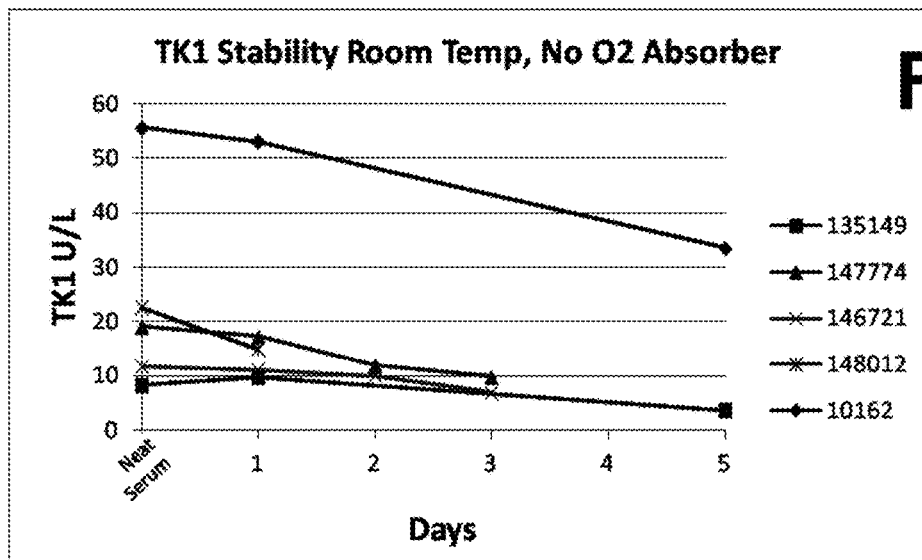
FIG. 6A is a plot diagram that summarizes the result of testing blood samples for TK 1 activity on five subjects over a period of five days.

FIG. 6A-6H show plots that summarize the results from testing TK1 in canine subjects. FIG. 6A is a plot diagram that summarizes the result of testing blood samples for TK 1 activity on five canine subjects over a period of five days. The samples were air dried and stored at room temperature and oxygen level was unmodified. The results presented in the plot of FIG. 6A confirm what was already known, namely, that TK1 activity declines in blood samples after days of storage. The results of FIG. 6A show that certain specimens decline faster than others making for a highly variable and unpredictable methodology unsuitable for laboratory testing.

Figure 6B:
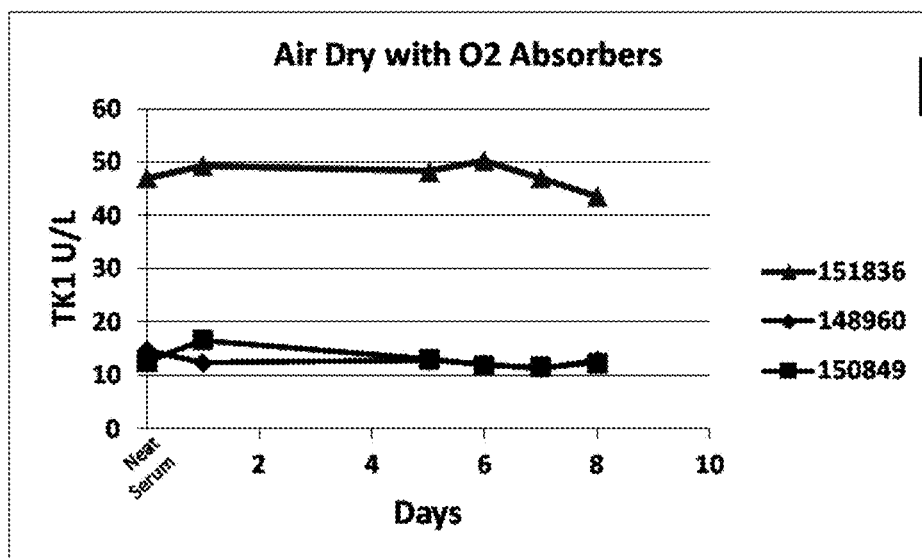
FIG. 6B is a plot diagram that summarizes the result data obtained in three (3) subjects over a period of 8 days.
Figure 6C:
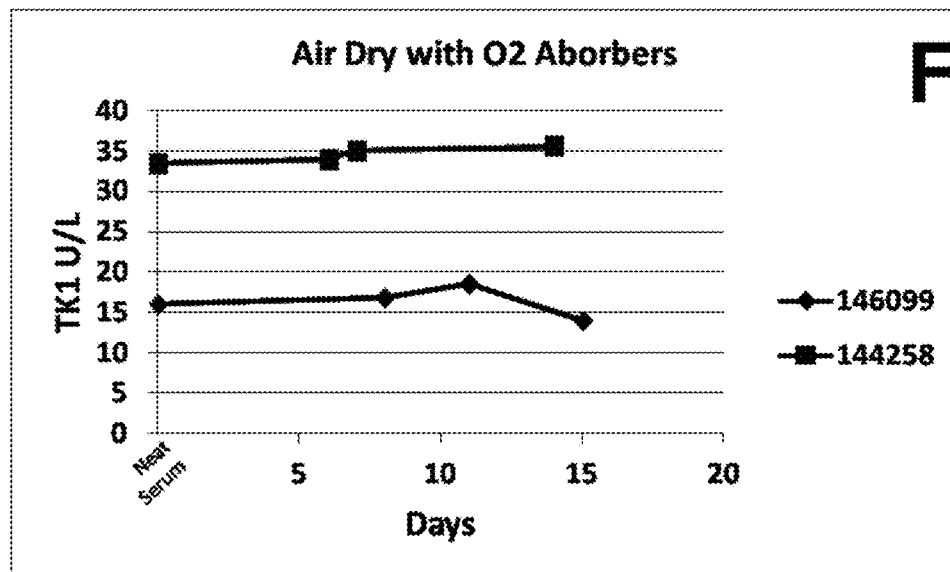
FIG. 6C is a plot diagram that summarizes the result of testing blood samples for TK1 activity in two (2) subjects using the method and system of the invention.
Figure 6D:
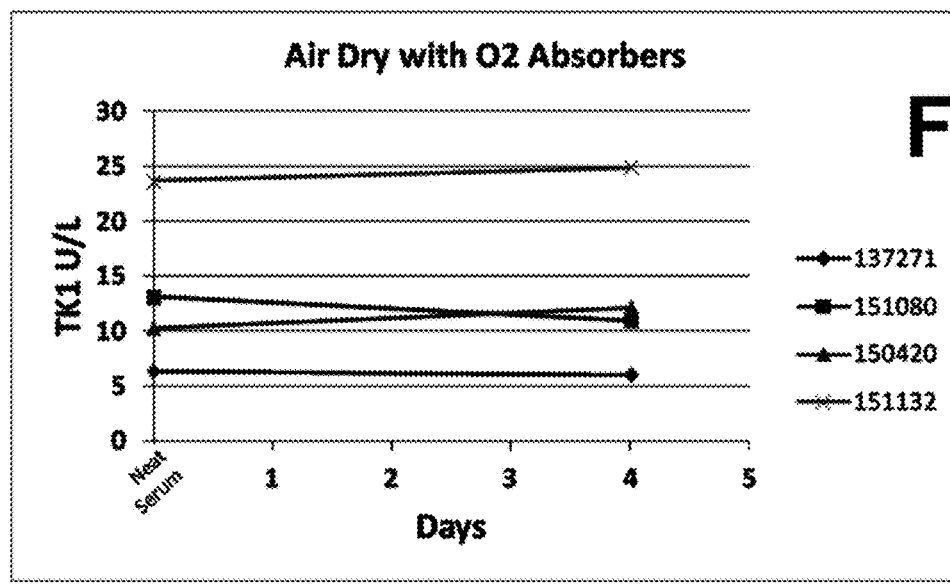
FIG. 6D is a plot diagram showing the result of TK1 activity test in four subjects.
Figure 6E:
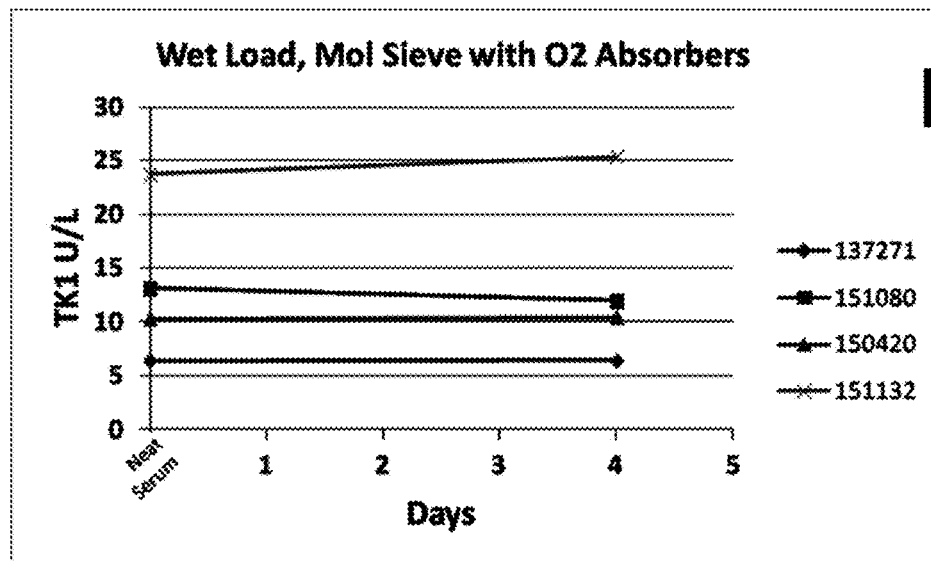
FIG. 6E is a plot diagram showing the result of TK1 activity test in four subjects from samples loaded into the O2-free MAP wet but with sufficient desiccant to absorb all moisture from the specimens.
Figure 6F:
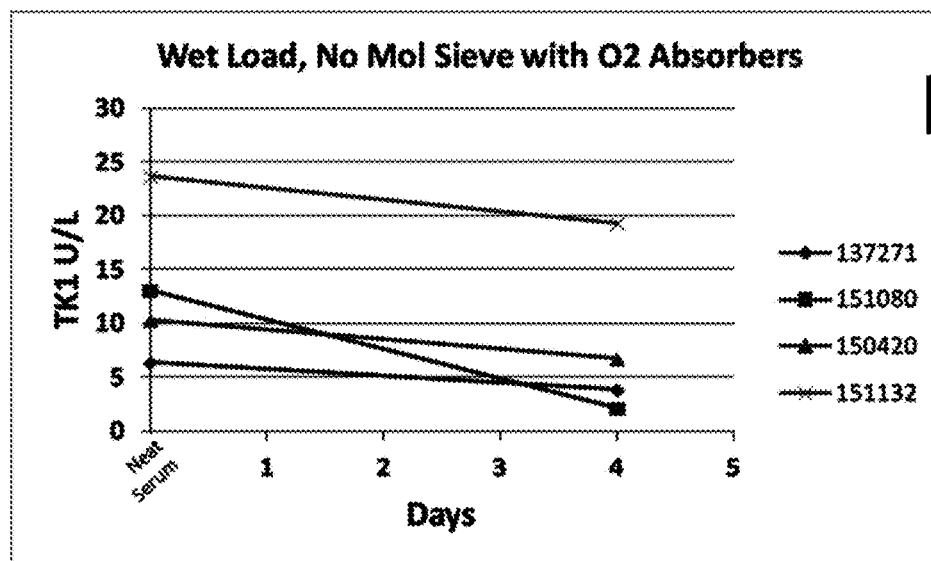
FIG. 6F is a plot diagram showing the result of TK1 activity test in four subjects from samples that were loaded into the $O_2$-free MAP wet but without any desiccant.
Figure 6G:
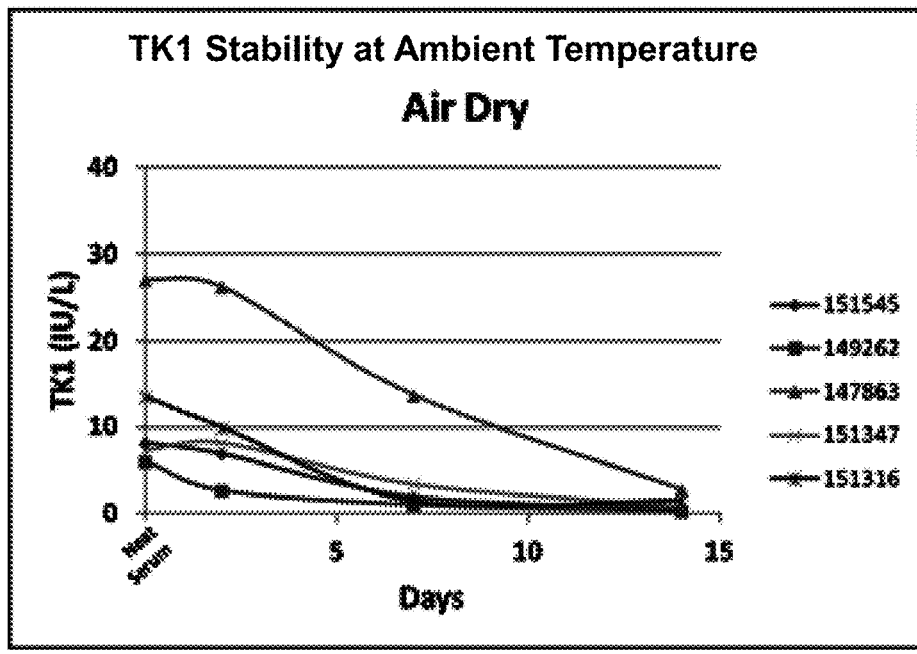
FIG. 6G shows the measurement of TK1 in five different subjects using prior art methods over a period of fourteen days.

FIG. 6G shows the measurement of TK1 in five different subjects using prior art methods to store blood sample over a period of fourteen days. The tests results represented in FIG. 6G were obtained from blood samples that were stored in the presence of a desiccant, but without altering the oxygen level.

FIG. 6B is a plot diagram that summarizes the result data obtained in three (3) subjects over a period of 8 days. FIG. 6B shows the results of measuring TK1 activity over time using an embodiment of the invention in three different patients at different time points up to 8 days.

FIG. 6C is a plot diagram that summarizes the result of testing blood samples for TK1 activity in two (2) subjects using the method and system of the invention. Following the methods of the invention, where samples were maintained in a MAP, free of oxygen and moisture, TK1 activity is maintained for up to 15 days at ambient temperature using embodiments of the invention.

In order to compare the effect of Moisture with/without Oxygen Absorption, more tests were carried out. The effect of moisture can be detrimental to the stability of analytes. Comparing 4 different patient samples stored for 4 days at ambient conditions under different conditions shows the degradation of TK1 when moisture is present even in the absence of $O_2$.

FIG. 6D is a plot diagram showing the result of TK1 activity test in four subjects. The samples were left to air dry and then placed in an O2-free MAP. The results show that there is no loss of signal in 4 days old samples.

FIG. 6E is a plot diagram showing the result of TK1 activity test in four subjects from samples loaded into the $O_2$-free MAP wet but with sufficient desiccant to absorb all moisture from the specimens. The results show that there is no loss of TK1 activity in 4 days old samples.

Figure 6H:
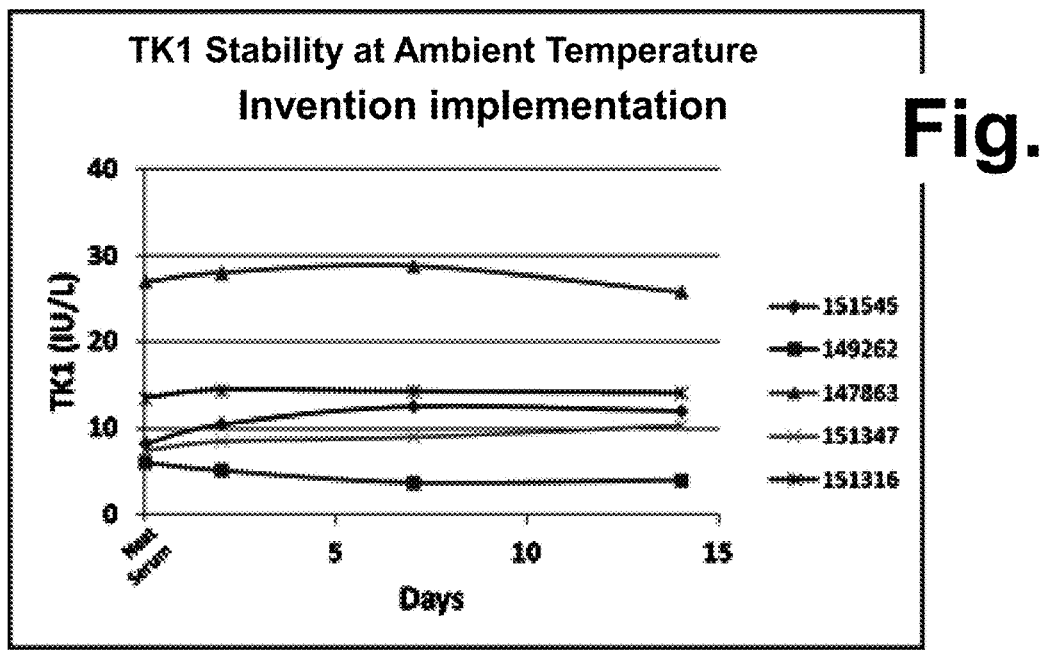
FIG. 6H shows the measurement of TK1 in same five subjects as in FIG. 6G using an implementation of the invention for storing blood samples for a period of fourteen days.

FIG. 6H shows the measurement of TK1 in five different subjects using an implementation of the invention for storing blood samples for a period of fourteen days. The latter results confirm that the blood sample that were stored in accordance with an implementation of the invention had a TK1 activity that remained constant after a period of fourteen days.

FIG. 6F is a plot diagram showing the result of TK1 activity test in four subjects from samples that were loaded into the $O_2$-free MAP wet but without any desiccant. The latter shows a substantial signal loss of TK1 activity in 4 days old samples. Table 1 summarizes the results of testing with TK1 for proof of concept.

TABLE 1

| FIG. | Absorbent Medium | Drying | $O_2$ Free | Outcome |
|---|---|---|---|---|
| 6A | Synthetic strips from Asante | Air | No | Failure |
| 6B | Synthetic strips from Asante | Air | Yes | Success |
| 6C | Synthetic strips from Asante | Air | Yes | Success |
| 6D | Synthetic VDI device | Air | Yes | Success |
| 6E | Synthetic VDI device | Molecular Sieve | Yes | Success |
| 6F | Synthetic VDI device | Wet | Yes | Failure |
| 6G | Synthetic VDI device | Air | No | Failure |
| 6H | Synthetic VDI device | Molecular Sieve | Yes | Success |

Enzymatic Tests.

Other Enzymatic Tests have been carried out to further test the utility of implementation of the invention in stabilizing blood sample for other analytes. Enzymes are particularly sensitive to drying and often show no or little activity. Further testing confirmed the efficacy of embodiments of the invention to preserve enzymatic activity for the plurality of selected enzymes for testing. Enzymatic activity was tested in blood sample from human subjects.

Figure 7:
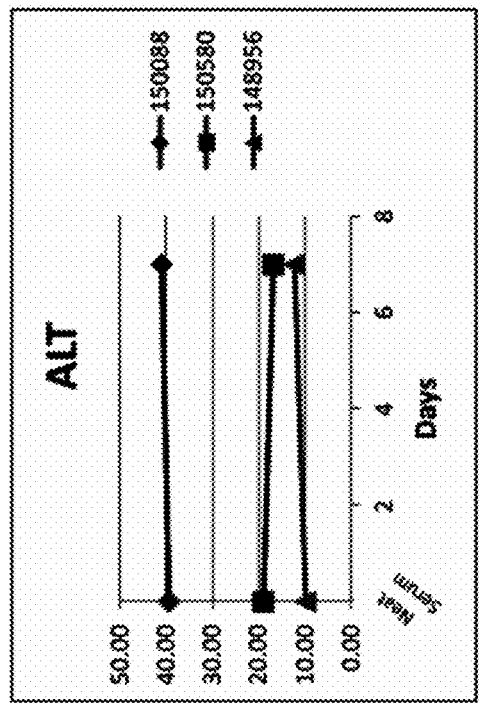
FIG. 7 is a plot diagram showing the result of Gamma-glutamyltransferase (GGT) activity test in three subjects from samples that were stored for a period of seven (7) days.

FIG. 7 is a plot diagram showing the result of Gamma-glutamyltransferase (GGT) activity test in three subjects from samples that were stored for a period of seven (7) days. The results show no loss of enzymatic activity after a period of seven days.

Figure 8:
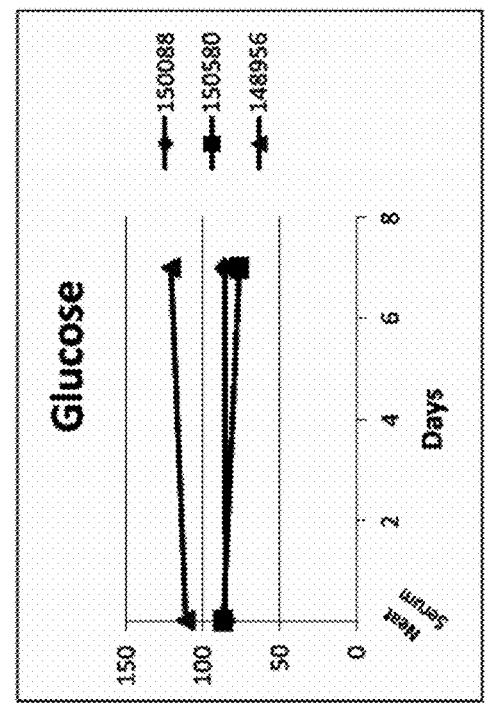
FIG. 8 is a plot diagram showing the result of Alanine transaminase (ALT) activity test in three subjects from samples that were stored for a period of seven (7) days.

FIG. 8 is a plot diagram showing the result of Alanine transaminase (ALT) activity test in three subjects from samples that were stored for a period of seven (7) days. The results show no loss of enzymatic activity of Alanine transaminase after a period of seven days.

Figure 9:
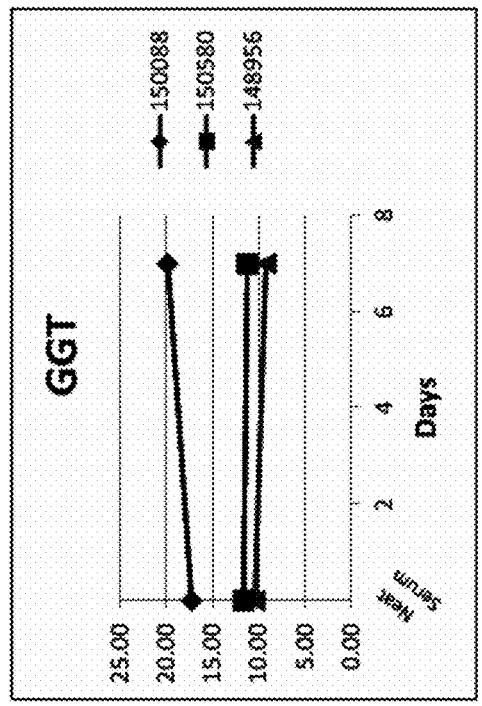
FIG. 9 is a plot diagram showing the result of aspartate aminotransferase (AST) activity test in three subjects from samples that were stored for a period of seven (7) days.

FIG. 9 is a plot diagram showing the result of aspartate aminotransferase (AST) activity test in three subjects from samples that were stored for a period of seven (7) days. The results show no loss of enzymatic activity of aspartate aminotransferase after a period of seven days.

Implementations of the invention were further tested with other analytes to further validate the utility of the implementations of the invention in stabilizing blood samples.

Figure 10:
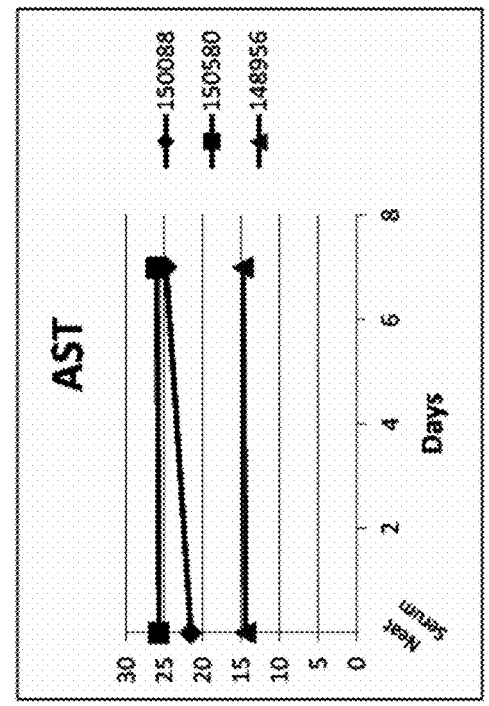
FIG. 10 is a plot diagram showing the result of glucose level in three subjects from samples that were stored for a period of seven (7) days.

FIG. 10 is a plot diagram showing the result of glucose level in three subjects from samples that were stored for a period of seven (7) days. The results show that the glucose levels remained stable after a period of seven days of storage.

Colorimetric Tests.

Following the methods of the invention, tests that are colorimetric in nature i.e, analyte/reagent that involve a chemical reaction, were carried out. Colorimetric tests have been carried out in blood samples from human subjects.

FIG. 11 is a plot diagram showing the result of testing blood urea nitrogen (BUN) level in three subjects from samples that were stored for a period of seven (7) days. The results show that the blood urea nitrogen (BUN) levels remained stable after a period of seven days of storage.

FIG. 12 is a plot diagram showing the result of testing blood creatinine level in three subjects from samples that were stored for a period of seven (7) days. The results show that the blood creatinine levels remained stable after a period of seven days of storage.

FIG. 13 is a plot diagram showing the result of testing blood albumin level in three subjects from samples that were stored for a period of seven (7) days. The results show that the blood albumin levels remained stable after a period of seven days of storage.

FIG. 14 is a plot diagram showing the result of testing blood total protein level in three subjects from samples that were stored for a period of seven (7) days. The results show that the blood total protein levels remained stable after a period of seven days of storage.

The results show that using embodiments of the invention, there is no deterioration in signal when testing for analytes using colorimetric tests. Chemical reactivity was maintained after 7 days at ambient temperature following the methods of the invention.

Calculated Tests.

To further test embodiments of the invention, tests of analytes that have sensitive relationships to one another, such as calculated values, have been carried out. The latter tests have carried on blood samples from human subjects.

Figure 15:
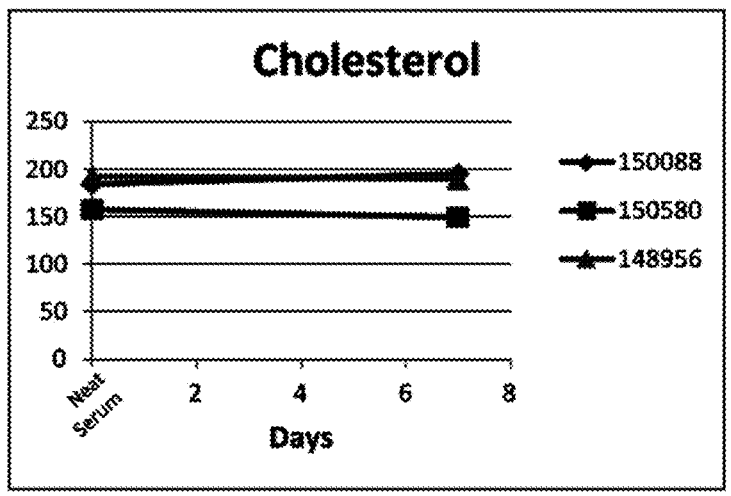
FIG. 15 is a plot diagram showing the result of testing blood cholesterol level in three subjects from samples that were stored for a period of seven (7) days.
Figure 16:
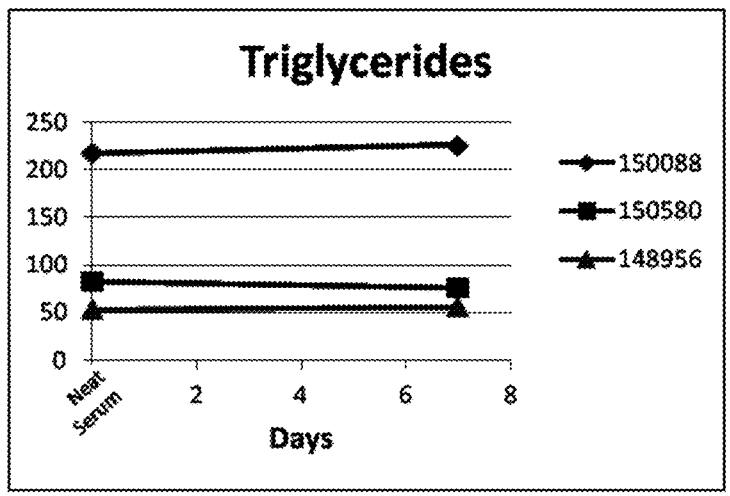
FIG. 16 is a plot diagram showing the result of testing blood triglycerides level in three subjects from samples that were stored for a period of seven (7) days.
Figure 17:
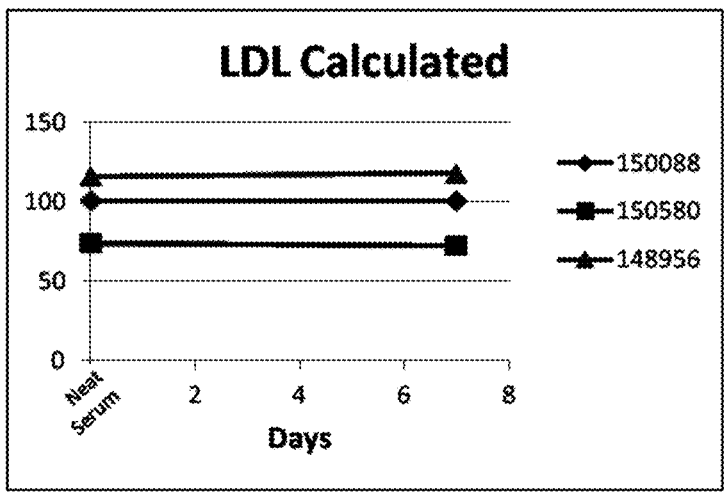
FIG. 17 is a plot diagram showing the result of testing blood low density lipoprotein (LDL) level in three subjects from samples that were stored for a period of seven (7) days.

Following the methods of the invention, tests have been carried out to measure cholesterol, triglycerides and low-density lipoprotein; the data for three individuals are presented in FIGS. 15, 16 and 17, respectively.

FIG. 15 is a plot diagram showing the result of testing blood cholesterol level in three subjects from samples that were stored for a period of seven (7) days. The results show that the blood cholesterol levels remained stable after a period of seven days of storage.

FIG. 16 is a plot diagram showing the result of testing blood triglycerides level in three subjects from samples that were stored for a period of seven (7) days. The results show that the blood triglycerides levels remained stable after a period of seven days of storage.

FIG. 17 is a plot diagram showing the result of testing blood low density lipoprotein (LDL) level in three subjects from samples that were stored for a period of seven (7) days. The results show that the blood LDL levels remained stable after a period of seven days of storage.

The results (as shown in FIGS. 15, 16 and 17) confirm that blood samples are preserved and that in the example of a lipid profile where LDL is a calculated parameter based on other measurements, the relationship is maintained after 7 days at ambient temperature following the methods of the invention.

Recovery Rate of Analytes

To further display the efficacy of implementations of the invention to preserve analytes in blood samples that have been stored. A serum portion was tested for TK1, Vitamin D, and C—reactive protein. The results are summarized in FIGS. 18, 19 and 20.

Figure 18:
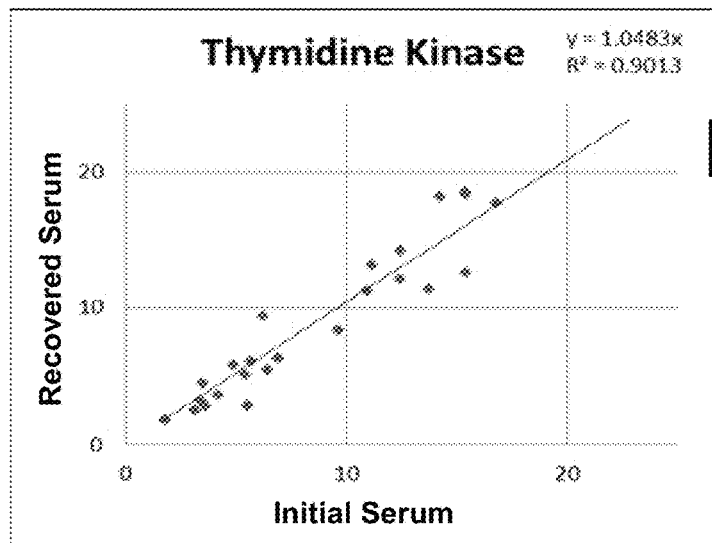
FIG. 18 is a plot diagram summarizing the test results of measuring TK1 in blood samples stored according to an embodiment of the invention.

FIG. 18 is a plot diagram summarizing the test results of measuring TK1 in canine subjects in blood samples stored according to an embodiment of the invention. Enzymatic TK1 levels were measured in serum samples obtained at the time blood samples were drawn (shown as the abscissa) and in recovered serum that was recovered after a period of storage (shown as ordinate). FIG. 18 shows that measurements made in recovered serum closely matched the initial measurement. The correlation is close to 1 (slope=1.056, $R^2$=0.90) indicating that no significant change has occurred in the measured enzymatic activity of TK1 after the period of storage.

Figure 19:
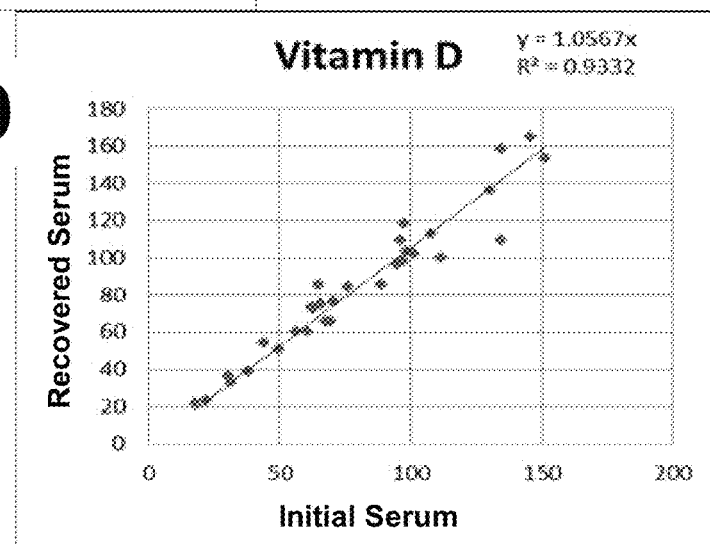
FIG. 19 is a plot diagram summarizing the test results of measuring vitamin D in blood samples stored according to an embodiment of the invention.

FIG. 19 is a plot diagram summarizing the test results of measuring vitamin D in canine subjects in blood samples stored according to an embodiment of the invention. Vitamin D levels were measured in serum samples obtained at the time blood samples were drawn (shown as the abscissa) and in recovered serum that was recovered after a period of storage (shown as ordinate). FIG. 19 shows that measurements made in recovered serum closely matched the initial measurement. The correlation is close to 1 (slope=1.056, $R^2$=0.93) indicating that no significant change has occurred in the measured level of vitamin D after the period of storage.

Figure 20:
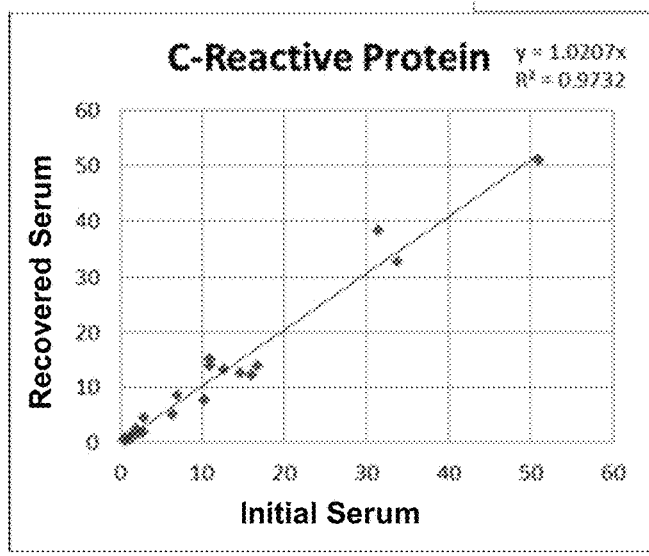
FIG. 20 is a plot diagram summarizing the test results of the concentration of C-reactive protein in blood samples stored according to an embodiment of the invention.

FIG. 20 is a plot diagram summarizing the test results of the concentration of C-reactive protein in canine subjects in blood samples stored according to an embodiment of the invention. C-reactive protein concentrations were measured in serum samples obtained at the time blood samples were drawn (shown as the abscissa) and in recovered serum that was recovered after a period of storage (shown as ordinate). FIG. 20 shows that measurements made in recovered serum closely matched the initial measurement. The correlation is close to 1 (slope=1.02, $R^2$=0.97) indicating that no significant change has occurred in the measured concentration of c-reactive protein after the period of storage.

Storage, Transportation and Shipping Requirements

As disclosed above, embodiments of the invention may be adapted to satisfy requirement of specific applications and/or storage means and shipping method. For example, embodiments of the invention may be adapted to fulfill the requirements of the United States postal service. The MAP, collection device, and stabilizers may adapted to meet the United States Postal Service (USPS) regulations for letter rates (201) and return letter, which may not, for example, exceed 11.5 inches in length, 6.125 inches in height, and 0.25 inches in thickness.

During transportation from the location of blood sampling to the test location, a package carrying the blood sample may be subjected to numerous physical factors. Parcels are typically protected with padding that absorbs mechanical shocks. However, temperature variation is almost unavoidable.

In the development of implementations of the invention, tests have been carried out to to check whether blood that has been stabilized in accordance with the invention could withstand substantial heat during transportation and storage. The protocol involved heating serum samples (e.g., to 35° C. or 50° C.) for a given period of time (e.g., 4 hours or 8 hours) then testing for an analyte (e.g., enzymatic activity of TK1), and comparing the results to data obtained from fresh serum. The protocol was further expanded by applying temperature variations. Serum samples, preserved in accordance with the invention, were subjected to high heat for a first period of time (e.g., 4 or 8 hours), then the temperature was reduced to room temperature for a second period of time (e.g., 1 hour), then the temperature was raised again for another period of time (e.g., 4 or 8 hours).

Table 2 summarizes the data obtained with blood samples from canine subjects, where TK1 was the analyte of choice. Room temperature is abbreviated as "RT", and all measurement of TK1 are expressed as Units per liter of TK1 activity.

Applicant tested transit conditions and the average temp was 30 C with brief periods of higher. For the latter reason, Applicant elected to test sample with treatment at 35° C. The test results as show in Table 2 are very good since they are clinically acceptable.

In the transit test, Applicant never detected temperatures as high as 50° C., however, the 50° C. was elected to simulate conditions that may be present, for example, in a mailbox in an area in the United States known for high summer temperatures. Even in that extreme condition, recovery was good only slightly less with 4 hrs at 50 C and still clinically relevant results with 16 hrs.

TABLE 2

| Subject ID | Initial | 4 hr | 8 hr | 4-1-4 hr | 8-1-8 hr |
|---|---|---|---|---|---|
| | RT | 35° C. | 35° C. | 35-RT-35° C. | 35-RT-35° C. |
| 152423 | 18.6 | 18.0 | 18.4 | 16.6 | 18.1 |
| 150147 | 23.4 | 23.8 | 24.4 | 22.1 | 22.8 |
| 150004 | 9.8 | 10.5 | 9.5 | 9.3 | 9.4 |
| | RT | 50° C. | 50° C. | 50-RT-50° C. | 50-RT-50° C. |
| 151930 | 9.4 | 7.7 | 7.7 | 8.7 | 4.2 |
| 151817 | 66.8 | 67.2 | 57.3 | 58.0 | 39.2 |

Thus a system for stabilizing analytes in blood samples for use in delayed extraction and tests in human and veterinary applications, comprising at least one device for holding a blood sample; a desiccant compound; a deoxygenation compound; and a sealable container for holding therewithin, a in sealed environment, said device for holding said blood sample, said desiccant compound and said deoxygenation compound.

The invention provides a method for stabilizing analytes in blood samples for delayed extraction and testing in human and veterinary blood tests, said method comprising obtaining a blood sample from a subject, placing said blood sample in a device for holding said blood sample, wherein said device comprises an absorbent paper, and placing said device for holding said blood sample into a sealable container; and providing a modified atmosphere environment within said sealable container by placing, into said sealable container, a desiccant compound to remove residual moisture and a deoxygenation compound to remove residual oxygen and sealing said sealable container to prevent fluid exchange between the interior and the exterior of said sealable container.

The invention provides a system for stabilizing analytes in blood samples for use in delayed extraction and tests in human and veterinary applications, said system comprising: a device for holding a blood sample; a desiccant compound; a deoxygenation compound; and a sealable container for holding there within, a in sealed environment, said device for holding said blood sample, said desiccant compound and said deoxygenation compound. The system, wherein said device for holding said blood sample further comprises an enclosure comprised of a first region for holding an absorbent medium and a second region for holding said desiccant compound, wherein said enclosure allows for free air circulation between said first region and said second region. The system, wherein said absorbent medium further comprises cellulose-based paper. The system, wherein said absorbent medium further comprises synthetic paper. The system, wherein said first region further having a hole that exposes a portion of said absorbent medium for allowing said blood sample to be directly deposited onto said portion of said absorbent medium. The system, wherein said first region and said second region are linked via a plurality of air circulation channels. The system, wherein said enclosure is comprised of two parts having a locking mechanism that allows the two parts to lock to one another to form a volume therewithin that forms at least said first region and said second region. The system, wherein said device for holding said blood sample, further comprises a dried blood spot device. The system, wherein said dried blood spot device further comprises cellulose-based cards. The system, wherein said dried blood spot device further comprises synthetic paper-based cards. The system, wherein said device for holding said blood sample, further comprises a fiber stick having an absorbent paper portion for absorbing a preset amount of blood. The system, wherein said device for holding said blood sample, further comprises a plurality of synthetic fiber wedges wherein each one of said plurality of wedges is configured to absorb a preset amount of blood. The system, wherein said desiccant further comprises a silica compound. The system, wherein said desiccant comprises a montmorillonite compound. The system, wherein said desiccant comprises a synthetic zeolite compound. The system, wherein said deoxygenation compound further comprises iron powder. The system, wherein said deoxygenation compound further comprises ascorbic acid. The system, wherein said deoxygenation compound further comprises an ascorbate salt. The system, wherein said deoxygenation compound further comprises catechol compound. The system, wherein said sealable container is made of impermeable material and further comprise tight closure for sealing the container to prevent fluid exchange between the interior and the exterior of said container. The system, wherein said sealable container further comprises a bag made of impermeable plastic, and further having a tight closure for sealing the bag. The system, wherein said sealable container further comprises a tight sealed box. The system, further comprises an extraction system comprising: a test tube further having an elevator; a centrifuge; and
 a buffer solution.

The invention provides a method for stabilizing analytes in blood samples for delayed extraction and testing in human and veterinary blood tests, said method comprising: obtaining a blood sample from a subject, placing said blood sample in a device for holding said blood sample, wherein said device comprises an absorbent medium, and placing said device for holding said blood sample into a sealable container; and providing a modified atmosphere environment within said sealable container by placing, into said sealable container, a desiccant compound to remove residual moisture and a deoxygenation compound to remove residual oxygen and sealing said sealable container to prevent fluid exchange between the interior and the exterior of said sealable container. The method further comprises placing said sealable container within a parcel for shipping via a postal service. The method, wherein said step of placing said blood sample in said device for holding said blood sample further comprises placing a plurality of fixed quantities of said blood sample on said absorbent medium contained within a dried blood spot card. The method, wherein said step of placing said blood sample in said device for holding said blood sample further comprises placing a fixed quantity of said blood sample on said absorbent medium contained within an enclosure, wherein said enclosure comprises a desiccant. The method, wherein said step of placing said blood sample in said device for holding said blood sample further comprises placing a plurality of fixed quantities of said blood sample on a cellulose paper based dried blood stick. The method of claim 25 further comprising extracting a recovered blood sample using the steps of: placing a portion of said absorbent medium of said device for holding said blood sample on top of an elevator placed within a sealable test tube containing a fixed quantity of a buffer solution, and sealing said test tube; inverting said test tube to immerse said portion of said absorbent medium into said buffer solution and incubating said test tube for at least one hour; and applying a centrifugal force on said test tube to extract most of said buffer solution from said portion of said absorbent medium.

The invention provides a system for stabilizing enzyme activity, protein site recognition by antibodies and chemical reactivity of hormones in blood samples for use in delayed extraction and tests in human and veterinary applications, said system comprising: a device for holding a blood sample; a desiccant compound;

a deoxygenation compound; and a sealable container for holding therewithin, a in sealed environment, said device for holding said blood sample, said desiccant compound and said deoxygenation compound. The system, wherein said device for holding said blood sample further comprises an enclosure comprised of a first region for holding an absorbent paper and a second region for holding said desiccant compound, wherein said enclosure allows for free air circulation between said first region and said second region. The system, wherein said device for holding said blood sample, further comprises a dried blood spot card. The system, wherein said dried blood spot card further comprises cellulose paper spots for holding a fixed quantity of blood. The system, wherein said dried blood spot card further comprises synthetic paper spots for holding a fixed quantity of blood. The system, wherein said desiccant further comprises a silica compound. The system, wherein said desiccant comprises a montmorillonite compound. The system, wherein said desiccant comprises a synthetic zeolite compound. The system, wherein said deoxygenation compound further comprises iron powder. The system, wherein said deoxygenation compound further comprises ascorbic acid. The system, wherein said deoxygenation compound further comprises an ascorbate salt. The system, wherein said deoxygenation compound further comprises catechol compound. The system, wherein said sealable container is made of impermeable material and further comprise tight closure for sealing the container to prevent fluid exchange between the interior and the exterior of said container. The system, wherein said sealable container further comprises a bag made of impermeable plastic, and further having a tight closure for sealing the bag. The system, wherein said sealable container further comprises a tight sealed box.

The invention provides a method for extracting blood samples from dried blood spots resulting in near neat-level blood samples, comprising: placing a test tube elevator in a sealable micro-centrifuge tube and a buffer solution in said sealable micro-centrifuge tube; obtaining at least one strip of absorbent paper from a dried blood holding device and placing said at least one strip in said sealable micro-centrifuge tube on top of said test tube elevator; incubating said strip of absorbent medium in said buffer solution inside by holding said micro-centrifuge tube flipped upside-down; and centrifuging said micro-centrifuge tube while directing the centrifugal force toward the bottom of said micro-centrifuge tube to push said buffer solution toward the bottom of said micro-centrifuge tube, while said at least strip of absorbent medium remains held by said test tube elevator close to the top of said micro-centrifuge tube. The method, wherein said obtaining said at least one strip further comprises obtaining paper punches. The method, wherein said obtaining said at least one strip further comprises obtaining paper rectangles. The method, wherein said obtaining said at least one strip further comprises obtaining paper wedges.

The invention provides a system for extracting blood samples from dried blood spots resulting in near neat-level blood samples, comprising: a sealable micro-centrifuge tube and a buffer solution in said sealable micro-centrifuge tube; a test tube elevator; at least one strip of absorbent paper obtained from a dried blood holding device; and a centrifuge. The system, wherein said test tube elevator has an elongated shape a first end of which rests against the bottom of said micro-centrifuge tube, and has a middle portion a cross section profile of which matches an inner section profile of said micro-centrifugal tube. The system, wherein said test tube elevator further has a second end that rests against a lid of said sealable micro-centrifugal tube. The system, wherein said at least one strip of absorbent paper further comprises at least one paper punch. The system, wherein said at least one strip of absorbent paper further comprises at least one paper rectangle.

What is claimed is:

1. A method for stabilizing analytes in blood samples, and for delayed extraction of blood samples from dried blood spots resulting in near neat-level blood samples for use in tests in human and veterinary applications, said method comprising steps of:

obtaining a blood sample from a subject, placing said blood sample in a device for holding said blood sample;

placing a test tube elevator in a sealable centrifuge tube and a buffer solution in a sealable centrifuge tube, wherein said test tube elevator includes a tubular portion vertically extended along a height of said sealable centrifuge tube and a planar portion perpendicular to said tubular portion and radially extended from said tubular portion toward an inner surface of said sealable centrifuge tube, wherein said planar portion is configured to divide said sealable centrifuge tube into an upper portion and a lower portion, and wherein said planar portion includes a plurality of holes for passing liquid between said lower and upper portions;

obtaining at least one strip of absorbent paper containing said blood sample from a dried blood holding device and placing said at least one strip of absorbent paper in said sealable centrifuge tube on top of said test tube elevator, wherein said at least one strip of absorbent paper is not in contact with a bottom of said sealable centrifuge tube;

incubating said at least one strip of absorbent paper in said buffer solution inside by holding said sealable centrifuge tube flipped upside-down; and centrifuging said sealable tube while directing a centrifuge force toward a bottom of said sealable centrifuge tube to push said buffer solution toward the bottom of said sealable centrifuge tube, while said at least one strip of absorbent paper remains held by said test tube elevator close to a top of said sealable centrifuge tube.

2. The method of claim 1, wherein in said step of placing said test tube elevator in said sealable centrifuge tube further comprises placing said test tube elevator in a sealable micro-centrifuge tube.

3. The method of claim 1, wherein said step of placing said blood sample in said device for holding said blood sample further comprises placing a plurality of fixed quantities of said blood sample on said at least one strip of absorbent paper contained within a dried blood spot card.

4. The method of claim 1, wherein said obtaining said at least one strip of absorbent paper further comprises obtaining paper punches.

5. The method of claim 1, wherein said obtaining said at least one strip of absorbent paper further comprises obtaining paper rectangles.

6. The method of claim 1, wherein said obtaining said at least one strip of absorbent paper further comprises obtaining paper wedges.

7. The method of claim 1 further comprising the steps of:
prior to obtaining said at least one strip of absorbent paper, placing said device for holding said blood sample into a sealable container; and
providing a modified atmosphere environment within said sealable container by placing, into said sealable container, a desiccant compound to remove residual moisture and deoxygenation compound to remove residual oxygen and sealing said sealable container to prevent fluid exchange between an interior and an exterior of said sealable container.

8. The method of claim 7 further comprises placing said sealable container within a parcel for shipping via a postal service.

\* \* \* \* \*